US006218513B1

(12) United States Patent
Anthony-Cahill et al.

(10) Patent No.: US 6,218,513 B1
(45) Date of Patent: Apr. 17, 2001

(54) GLOBINS CONTAINING BINDING DOMAINS

(75) Inventors: Spencer J. Anthony-Cahill, Bellingham, WA (US); Janet K. Epp, Boulder, CO (US); Bruce A. Kerwin, Lafayette, CO (US); Peter O. Olins, Superior, CO (US); Antony J. Mathews, Auckland (NZ)

(73) Assignee: Baxter Biotech Technology Sarl, Neuchatel (CH)

( * ) Notice: Subject to any disclaimer, the term of this patent is extended or adjusted under 35 U.S.C. 154(b) by 0 days.

(21) Appl. No.: 09/091,814

(22) PCT Filed: Dec. 20, 1996

(86) PCT No.: PCT/US96/20632

§ 371 Date: Jun. 22, 1998

§ 102(e) Date: Jun. 22, 1998

(87) PCT Pub. No.: WO97/23631

PCT Pub. Date: Jul. 3, 1997

Related U.S. Application Data
(60) Provisional application No. 60/021,001, filed on Dec. 22, 1995, now abandoned.

(51) Int. Cl.[7] .......................... A61K 35/14; A61K 38/00
(52) U.S. Cl. ........................ 530/380; 530/385; 530/386; 530/350; 514/2; 424/192.1; 424/193.1
(58) Field of Search ..................................... 530/380, 350, 530/829, 385, 386; 514/2; 424/192.1, 193.1

(56) References Cited

U.S. PATENT DOCUMENTS

| Re. 34,271 | 6/1993 | Walder . | |
|---|---|---|---|
| 4,001,200 | 1/1977 | Bonsen et al. | 530/385 |
| 4,001,401 | 1/1977 | Bonsen et al. | 514/6 |
| 4,053,590 | 10/1977 | Bonsen et al. | 514/6 |
| 4,336,248 | 6/1982 | Bonhard et al. | 530/354 |
| 4,343,715 | 8/1982 | Bonaventura et al. | 252/186.33 |
| 4,529,719 | 7/1985 | Tye . | |
| 4,584,130 | 4/1986 | Bucci et al. | 530/385 |
| 4,769,326 | 9/1988 | Rutter | 435/68.1 |
| 4,826,811 | 5/1989 | Sehgal et al. . | |
| 5,028,588 | 7/1991 | Hoffman et al. . | |
| 5,084,558 | 1/1992 | Rausch et al. . | |
| 5,194,590 | 3/1993 | Sehgal et al. . | |
| 5,239,061 | 8/1993 | Fronticelli et al. . | |
| 5,296,465 | 3/1994 | Rausch et al. . | |
| 5,320,965 | 6/1994 | Chiang | 436/11 |
| 5,449,759 | 9/1995 | Hoffman et al. . | |

FOREIGN PATENT DOCUMENTS

| WO8809179 | 12/1988 | (WO) . |
|---|---|---|
| WO9013645 | 11/1990 | (WO) . |
| WO9116349 | 11/1991 | (WO) . |
| WO 91/19505 * | 12/1991 | (WO) . |
| WO9211283 | 7/1992 | (WO) . |
| WO9222646 | 12/1992 | (WO) . |
| WO9309143 | 5/1993 | (WO) . |
| WO9422482 | 10/1994 | (WO) . |
| WO9514038 | 7/1995 | (WO) . |
| WO9613583 | 5/1996 | (WO) . |
| 9627388 | 9/1996 | (WO) . |

OTHER PUBLICATIONS

Riggs; "Hemoglobin Polymerization in Mice"; Science 147:621–623 (1965).

Bonaventura et al.; "Polymerization of Hemoglobins of Mouse and Man: Structural Basis"; Science 149:800–802 (1967).

Tondo et al; "Functional Properties of Hemoglobin Pôrto Alegre ($\alpha_2^A\beta_2^{9Ser \to Cys}$) and the Reactivity of its Extra Cysteinyl Residue"; Biochem. Biophys. Acta 342:15–20 (1974).

Green; "Avidin"; Adv. Protein Chem.; 29:85–133 (1975).

Ishimoto et al.; "A Variant Hemoglobin Found in *Macaca fuscata*: Another Polymerizing Hemoglobin of Macaques"; J. Anthrop. Soc. Nippon 83:233–243 (1975).

Takenaka; "Hemoglobin IZU(MACACA): β83 (EF 7) Gly→Cys. A New Hemoglobin Variant Found in the Japanese Monkey (*Macaca fuscata*)"; Biochem. Biophys. Acta 492:433–444 (1977).

Pietenpol et al.; "Sequence-specific Transcriptional Activation is essential for Growth Suppression by p53"; Proc. Natl. Acad. Sci. USA 91:1998–2002 (1984).

White et al.; "Toxicity of Human Hemoglobin Solution infused into Rabbits"; J. Lab. Clin. Med. 108:121–131 (1986).

Tam et al.; "The Hemoglobins of the Bullfrog *Rana catesbeiana*"; J. Biol. Chem. 261:8290–8294 (1986).

Argarana et al.; "Molecular Cloning and Nucleotide Sequence of the Streptavidin Gene"; Nucl. Acids Rs. 14:1871–1882 (1986).

Tondo; "Osmometric Study of the Subunit Dissociation of Hemoglobin Porto Alegre [β9(A6)Ser→Cys] Dissulfide Polymer"; An. Acad. Bras. Ci. 59:243–251 (1987).

Adams et al.; "HB Mississippi [β44(CD3)Ser→Cys]: A New Variant with Anomalous Properties"; Hemoglobin 11:435–452 (1987).

Landschultz et al.; "The Leucine Zipper: A Hypothetical Structure Common to a New Class of DNA Binding Proteins"; Science 240:1759–1764 (1988).

(List continued on next page.)

Primary Examiner—Phillip Gambel
Assistant Examiner—Marianne DiBrino
(74) Attorney, Agent, or Firm—Senniger, Powers, Leavitt & Roedel

(57) ABSTRACT

The present invention relates to globins containing non-naturally occurring binding domains, In particular, the present invention is directed toward a binding domain comprising the oligomerizing domain GCN4 and GCN4 derivatives. The present invention also relates to multimeric hemoglobins comprised of at least one globin containing at least one non-naturally occurring binding domain.

10 Claims, No Drawings

OTHER PUBLICATIONS

Hallewell et al.; "Genetically Engineered Polymers of Human CuZn Superoxide Dismutase"; J. Biol. Chem. 264:5260–5268 (1989).

O'Shea et al.; "Preferential Heterodimer Formation by Isolated Leucine Zippers from Fos and Jun"; Science 245:646–648 (1989).

Vlahakes et al.; "Hemodynamic Effects and Oxygen Transport Properties of a New Blood Substitute in a Model of Massive Blood Replacement"; J. Thorac. Cardiovas. Surg. 100:379–388 (1990).

O'Neil et al.; "Design of DNA–Binding Peptides Based on the Leucine Zipper Motif"; Science 249:774–778 (1990).

Hu et al.; "Sequence Requirements for Coiled–Coils: Analysis with λ Repressor–GCN4 Leucine Zipper Fusions"; Science 250:1400–1403 (1990).

Hodges et al.; "Synthetic Model Proteins: Contribution of Hydrophobic Residues and Disulfide Bonds to Protein Stability"; Peptide Res. 3:123–137 (1990).

Argos; "An Investigation of Oligopeptides Linking Domains in Protein Tertiary Structures and Possible Candidates for General Gene Fusion"; J. Mol. Biol. 211:943–958 (1990).

Komiyama et al.; "Was the Loss of the D Helix in α Globin a functionally Neutral Mutation?"; Nature 352:349–351 (1991).

O'Shea et al.; "X–ray Structure of the GCN4 Leucine Zipper, a Two–Stranded, Parallel Coiled Coil"; Science 254:539–544 (1991).

Vandegriff; "Blood Substitutes: Engineering the Haemoglobin Molecule"; Biotechnology and Genetic Engineering Rev. 10:403–453 (1992).

Stürzbecher et al.; "A C–Terminal α–helix Plus Basic Region Motif is the Major Structural Determinant of p53 Tetramerization"; Oncogene 7:1513–1523 (1992).

Mörgelin; "Electron Microscopy of native Cartilage Oligomeric Matrix Protein Purified from the Swarm Rat Chondrosarcoma Reveals a Five–Armed Structure"; J. Biol. Chem. 267:6137–6141 (1992).

Anthony–Cahill et al.; "Molecular Characterization of Helix–Loop–Helix Peptides"; Science 255:979–983 (1992).

Pack et al.; "Miniantibodies: Use of Amphipathic Helices to Produce Functional, Flexibly Linked Dimeric $F_v$ Fragments with High Avidity in Escherichia coli"; Biochemistry 31:1579–1584 (1992).

Zhu et al.; Design, Synthesis and Structural Characterization of Model Heterodimeric Coiled–Coil Proteins; Int. J. Peptide Protein Res. 40:171–179 (1992).

Yamano et al.; "In Vivo Biotinylation of Fusion Proteins Expressed in Escherichia coli with a Sequence of Propionibacterium freudenreichii Transcarboxylase 1.3S Biotin Subunit"; Biosci. Biotechnol. Biochem. 56:1017–1026 (1992).

Weber et al.; "Crystal Structure and Ligand–Binding Studies of a Screened Peptide Complexed with Streptavidin"; Biochemistry 31:9350–9354 (1992).

Oldberg et al.; "COMP (Cartilage Oligomeric Matrix Protein) is Structurally Related to the Thrombospondins"; J. Biol. Chem. 267:22346–22350 (1992).

Looker et al.; "A Human Recombinant Haemoglobin Designed for use as a Blood Substitute"; Nature 356:258–260 (1992).

Livnah et al.; "Three–dimensional Structures of Avidin and the Avidin–Biotin Complex"; Proc. Natl. Acad. Sci. USA 90:5076–5080 (1993).

Neuhold et al.; "HLH Forced Dimers: Tethering MyoD to E47 Generates a Dominant Positive Myogenic Factor Insulated from Negative Regulation by Id", Cell 74:1033–1042 (1993).

Holliger et al.; "'Diabodies': Small Bivalent and Bispecific Antibody Fragments"; Proc. Natl. Acad. Sci USA 90:6444–6448 (1993).

Saggio et al.; "Biotin Binders Selected from a Random Peptide Library Expressed on Phage"; Biochem. J. 293:613–616 (1993).

Schmidt et al.; "The Random Peptide Library–Assisted Engineering of a C–Terminal Affinity Peptide, Useful for the Detection and Purification of a Functional Ig Fv Fragment"; Protein Eng._6:109–122 (1993).

Harbury et al.; "A Switch Between Two–, Three– and Four–Stranded Coiled Coils in GCN4 Leucine Zipper Mutants"; Science 262:1401–1407 (1993).

Pavletich et al.; "The DNA–Binding Domain of p53 Contains the Four Conserved Regions and the Major Mutation Hot Spots"; Genes & Devel. 7:2556–2564 (1993).

McWhirter et al.; "A Coiled–Coil Oligomerization Domain of Bcr is Essential for the Transforming Function of Bcr–Abl Oncoproteins"; Mol. Cell. Biol. 13:7587–7595 (1993).

Spahn et al.; "Cardiovascular and Coronary Physiology of Acute Isovolemic Hemodilution: A Review of Nonoxygen––Carrying and Oxygen–Carrying Solutions"; Aneth. Analg. 78:1000–1021 (1994).

Efimov et al.; "The Thrombospondin–like Chains of Cartilage Oligomeric Matrix Protein are Assembled by a Five–Stranded α–helical Bundle Between Residues 20 and 83"; FEBS Letters 341:54–58 (1994).

Kolatkar et al.; "Structural Analysis of Urechis caupo Hemoglobin"; J. Mol. Biol. 237:87–97 (1994).

Chapman–Smith et al.; "Expression, Biotinylation and Purification of a Biotin–Domain Peptide from the Biotin Carboxy Carrier Protein of Escherichia coli Acetyl–CoA Carboxylase"; Biochem. J. 302:881–887 (1994).

Leon–del–Rio et al.; "Sequence Requirements for the Biotinylation of Carboxyl–Terminal Fragments of Human Propionyl–CoA Carboxylase α Subunit Expressed in Escherichia coli"; J. Biol. Chem. 269:22964–22968 (1994).

Newton et al.; "Characterization of Human and Mouse Cartilage Oligomeric Matrix Protein"; Genomics 24:435–439 (1994).

Pack et al.; "Tetravalent Miniantibodies with High Avidity Assembling in Escherichia coli"; J. Mol. Biol. 246:28–34 (1995).

Waldburger et al.; "Domains of Mnt Repressor: Roles in Tetramer Formation, Protein Stability, and Operator DNA Binding"; Biochemistry 34:13109–13116 (1995).

Clore et al.; "Refined Solution Structure of the Oligomerization Domain of Tumour Suppressor p53"; Nature Struct. Biol. 2:321–333 (1995).

Jeffrey et al.; "Crystal Structure of the Tetramerization Domain of the p53 Tumor Suppressor at 1.7 Angstroms"; Science 267:1498–1502 (1995).

Milla et al.; "P22 Arc Repressor: Transition State Properties Inferred from Mutational Effects on the Rates of Protein Unfolding and Refolding"; Biochemistry 34:13914–13919 (1995).

Rheinnecker et al.; "Multivalent Antibody Fragments with High Functional Affinity for a Tumor–Associated Carbohydrate Antigen"; J. Immunol. 157:2989–2997 (1996).

Lumb et al.; "A Buried Polar Interaction Imparts Structural Uniqueness in a Designed Heterodimeric Coiled Coil"; Biochemistry 34:8642–8648 (1995).

Mekelberger et al.; "Dendrimers, Arborols, and Cascade Molecules: Breakthrough into Generations of New Materials"; Angewante Chemie, Int. Ed. Engl. 31:1571–1576 (1992).

Ngo et al. The Protein Folding Problem and Tertiary Structure Prediction. pp. 491–495, 1994.*

* cited by examiner

SEQUENCE LISTING

```
<160> NUMBER OF SEQ ID NOS: 116

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:Amino Acid
      Linker

<400> SEQUENCE: 1

Gly Gly Gly Gly Ser
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:Amino Acid
      Linker

<400> SEQUENCE: 2

Gly Gly Gly Ser
 1

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Mutagenisis
      Seq.

<400> SEQUENCE: 3
accgttctga ctagtaaata ccgttaatga                                       30

<210> SEQ ID NO 4
<211> LENGTH: 30
<212> TYPE: DNA
```

-continued

```
<213> ORGANISM: Artificial Sequence
<220> FEATURE:
<223> OTHER INFORMATION: Description of Artificial Sequence: Mutagenisis
      Seq.

<400> SEQUENCE: 4
ggaggttaat taatgctgtc tcctgcagat                                        30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Mutagenisis
      Seq.

<400> SEQUENCE: 5
ctggtgggta agttctggt ttgcgttctg                                         30

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence:peptide
      linker

<400> SEQUENCE: 6
ctagtaaata ccgatcgggt ggctctggcg gttctgttct gtctcctgca                  50

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:peptide
      linker

<400> SEQUENCE: 7
ggagacagaa cagaaccgcc agagccaccc gatcggtatt ta                          42

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Amino Acid
      Linker

<400> SEQUENCE: 8

Gly Gly Ser Gly Gly Ser Gly Gly Ser Gly Gly Ser Gly Gly
 1               5                  10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Amino Acid
      linker

<400> SEQUENCE: 9

Ser Gly Gly Ser Gly Gly Ser Gly Gly Ser Gly Gly Ser Gly Gly Ser
 1               5                  10                  15

<210> SEQ ID NO 10
<211> LENGTH: 68
```

```
<212> TYPE: DNA
<213> ORGANISM: Artificial Sequence
<220> FEATURE:
<223> OTHER INFORMATION: Description of Artificial Sequence: Restriction
      site Oligonucleotide

<400> SEQUENCE: 10
gggccgcctt aagtacccgg gtttctgcag aaagcccgcc taatgagcgg gcttttttt      60 ccttaggg                                                              68

<210> SEQ ID NO 11
<211> LENGTH: 67
<212> TYPE: DNA
<213> ORGANISM: Artificial Sequence
<220> FEATURE:
<223> OTHER INFORMATION: Description of Artificial Sequence: Restriction
      site Oligonucleotide

<400> SEQUENCE: 11
gatcccctaa ggaaaaaaaa gcccgctcat ttaggcgggc tttctgcaga aacccgggta      60
cttaagg                                                               67

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: GCN4 Linker
      Top Strand

<400> SEQUENCE: 12
ctagtaaata ccgtggtggt tctggtggtt ctggtggttc tggcggcc                  48

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: GCN4 Top
      Strand

<400> SEQUENCE: 13
gcctgaaaca gctggaagac aaactggaag aactgctgtc taaactgtac                50

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: GCN4 Top
      Strand

<400> SEQUENCE: 14
cacctggaaa acgaactggc tcgtcttaag aaactgtgcg gtgaacgtgg t              51

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: GCN4 Top
      Strand

<400> SEQUENCE: 15
ggttctggtg gttctggtgg ttctggtggt gttctgtctc ctgca                     45
```

```
<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: GCN4 Bottom
      Strand

<400> SEQUENCE: 16
ggagacagaa caccaccaga accaccagaa ccaccagaac cacca              45

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: GCN4 Bottom
      Strand

<400> SEQUENCE: 17
cgttcaccgc acagtttctt aagacgagcc agttcgtttt ccaggtggta ca      52

<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence: GCN4 Bottom
      Strand

<400> SEQUENCE: 18
gtttagacag cagttcttcc agtttgtctt ccagctgttt caggcggcc          49

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: GCN4 Bottom
      Strand

<400> SEQUENCE: 19
gccagaacca ccagaaccac cagaaccacc acggtattta                    40

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: GCN4 Top
      Strand no Cysteine

<400> SEQUENCE: 20
cacctggaaa acgaactggc tcgtcttaag aaactgctgg gtgaacgtgg t       51

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: GCN4 Bottom
      Strand No Cysteine

<400> SEQUENCE: 21
cgttcaccca gcagtttctt aagacgagcc agttcgtttt ccaggtggta ca      52
```

```
<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: polymerase
      chain reaction oligos

<400> SEQUENCE: 22
cgcactagta ataccgtgg t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: polymerase
      chain reaction oligos

<400> SEQUENCE: 23
cgcctgcagg agacagaaca c                                             21

<210> SEQ ID NO 24
<211> LENGTH: 64
<212> TYPE: PRT
<213> ORGANISM: Artificial Sequence
<220> FEATURE:
<223> OTHER INFORMATION: Description of Artificial Sequence: GCN4 with
      Cys

<400> SEQUENCE: 24

Thr Ser Lys Tyr Arg Gly Gly Ser Gly Gly Ser Gly Gly Ser Gly Gly
 1               5                  10                  15

Arg Leu Lys Gln Glu Asp Lys Leu Glu Glu Leu Leu Ser Lys Leu Tyr
                20                  25                  30

His Leu Glu Asn Glu Leu Ala Arg Leu Lys Leu Cys Gly Glu Arg Gly
            35                  40                  45

Gly Ser Gly Gly Ser Gly Gly Ser Gly Gly Val Leu Ser Pro Ala Asp
        50                  55                  60

<210> SEQ ID NO 25
<211> LENGTH: 64
<212> TYPE: PRT
<213> ORGANISM: Artificial Sequence
<220> FEATURE:
<223> OTHER INFORMATION: Description of Artificial Sequence: GCN4 no Cys

<400> SEQUENCE: 25

Thr Ser Lys Tyr Arg Gly Gly Ser Gly Gly Ser Gly Gly Ser Gly Gly
 1               5                  10                  15

Arg Leu Lys Gln Glu Asp Lys Leu Glu Glu Leu Leu Ser Lys Leu Tyr
                20                  25                  30

His Leu Glu Asn Glu Leu Ala Arg Leu Lys Leu Leu Gly Glu Arg Gly
            35                  40                  45

Gly Ser Gly Gly Ser Gly Gly Ser Gly Gly Val Leu Ser Pro Ala Asp
        50                  55                  60

<210> SEQ ID NO 26
<211> LENGTH: 47
<212> TYPE: PRT
<213> ORGANISM: Artificial Sequence
<220> FEATURE:
<223> OTHER INFORMATION: Description of Artificial Sequence:Amino Acid
      linker and coiled coil
```

<400> SEQUENCE: 26

Ser Lys Tyr Arg Pro Lys Pro Ser Thr Pro Pro Gly Ser Ser Arg Leu
 1               5                  10                  15

Lys Gln Leu Glu Asp Lys Leu Glu Glu Leu Leu Ser Lys Leu Tyr His
                20                  25                  30

Leu Glu Asn Glu Leu Ala Arg Leu Lys Lys Leu Cys Gly Glu Arg
            35                  40                  45

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 27
ctagtaaata ccgtccgaaa ccatctaccc cgccgggctc ttctc            45

<210> SEQ ID NO 28
<211> LENGTH: 53
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 28
gtctgaaaca gctggaagat aaactggaag aactgctgag caaactgtac cac            53

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 29
ctggaaaacg aactggctcg tctgaaaaaa ctgtgcggtg aac            43

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 30
gttaatgatc tagataagga ggtaaatata tgcacctgac t            41

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 31
ccggagtcag gtgcatatat ttacctcctt at            32

<210> SEQ ID NO 32
<211> LENGTH: 41

```
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 32
ctagatcatt aacgttcacc gcacagtttt ttcagacgag c                  41

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: Synthetic
      oligomer for cassette construct

<400> SEQUENCE: 33
cagttcgttt tccaggtggt acagtttgct cagcagttct tccagtttat cttccag    57

<210> SEQ ID NO 34
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligomer for cassette construct

<400> SEQUENCE: 34
ctgtttcaga cgagaagagc ccggcggggt agatggtttc ggacggtatt ta         52

<210> SEQ ID NO 35
<211> LENGTH: 48
<212> TYPE: PRT
<213> ORGANISM: Artificial Sequence
<220> FEATURE:
<223> OTHER INFORMATION: Description of Artificial Sequence: Amino acid
      sequence of the domain coded by cassette

<400> SEQUENCE: 35

Thr Ser Lys Tyr Arg Pro Lys Pro Ser Thr Pro Pro Gly Ser Ser Arg
  1               5                  10                  15

Leu Lys Gln Leu Glu Asp Lys Leu Glu Glu Leu Leu Ser Lys Leu Tyr
             20                  25                  30

His Leu Glu Asn Glu Leu Ala Arg Leu Lys Lys Leu Cys Gly Glu Arg
         35                  40                  45

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence:  P53 Top
      Strand

<400> SEQUENCE: 36
ctagtaaata ccgtggtggt tctgtgtggt tctggtggtt ctggtggtaa cacctctt   58

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence:  P53 Top
      Strand

<400> SEQUENCE: 37
```
cttctccgca gccgaaaaaa aaaccgctgg acggtgagta cttcaccctg caaatcc        57

<210> SEQ ID NO 38
<211> LENGTH: 57
<212> TYPE: DNA
<213> ORGANISM: Artificial Sequence
<220> FEATURE:
<223> OTHER INFORMATION: Description of Artificial Sequence:  P53 Top
      Strand

<400> SEQUENCE: 38
gtggtcgtga acgtttcgag atgtttcgcg aactgaacga agctctggaa cttaagg        57

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence:  P53 Top
      Strand

<400> SEQUENCE: 39
acgctcaggc ttaatgctct agataaggag gtaaatatat gcacctgact        50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: P53 Bottom
      Strand

<400> SEQUENCE: 40
ccggagtcag gtgcatatat ttacctcctt atctagatca ttaagcctga        50

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: P53 Bottom
      Strand

<400> SEQUENCE: 41
gcgtccttaa gttccagagc ttcgttcagt tcgcgaaaca tctcgaaacg ttcacga        57

<210> SEQ ID NO 42
<211> LENGTH: 57
<212> TYPE: DNA
<213> ORGANISM: Artificial Sequence
<220> FEATURE:
<223> OTHER INFORMATION: Description of Artificial Sequence: P53 Bottom
      Strand

<400> SEQUENCE: 42
ccacggattt gcagggtgaa gtactcaccg tccagcggtt ttttttcgg ctgcgga        57

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: P53 Linker
      Bottom Strand

<400> SEQUENCE: 43
gaagaagagg tgttaccacc agaaccacca gaaccaccag aaccaccacg gtattta    57

```
<210> SEQ ID NO 44
<211> LENGTH: 72
<212> TYPE: PRT
<213> ORGANISM: Artificial Sequence
<220> FEATURE:
<221> NAME/KEY: SITE
<222> LOCATION: (61)..(62)
<223> OTHER INFORMATION: End- Break in strand
<220> FEATURE:
<221> NAME/KEY: SITE
<222> LOCATION: (63)..(64)
<223> OTHER INFORMATION: End- Break in strand
<220> FEATURE:
<223> OTHER INFORMATION: Description of Artificial Sequence: Amino acid
      encoded by P53 cassette domain
```

<400> SEQUENCE: 44

Thr Ser Lys Tyr Arg Gly Gly Ser Gly Gly Ser Gly Gly Ser Gly Gly
 1               5                  10                  15

Asn Thr Ser Ser Ser Pro Gln Pro Lys Lys Lys Pro Leu Asp Gly Glu
            20                  25                  30

Tyr Phe Thr Leu Gln Ile Arg Gly Arg Glu Arg Phe Glu Met Phe Arg
        35                  40                  45

Glu Leu Asn Glu Ala Leu Glu Leu Lys Asp Ala Gln Ala Ser Arg Gly
    50                  55                  60

Gly Tyr Met His Leu Thr Pro Glu
65                  70

```
<210> SEQ ID NO 45
<211> LENGTH: 64
<212> TYPE: PRT
<213> ORGANISM: Artificial Sequence
<220> FEATURE:
<223> OTHER INFORMATION: Description of Artificial Sequence: Murine comp
      domain
```

<400> SEQUENCE: 45

Gln Gly Gln Ile Pro Leu Gly Gly Asp Leu Ala Pro Gln Met Leu Arg
 1               5                  10                  15

Glu Leu Gln Glu Thr Asn Ala Ala Leu Gln Asp Val Arg Glu Leu Leu
            20                  25                  30

Arg Gln Gln Val Lys Glu Ile Thr Phe Leu Lys Asn Thr Val Met Glu
        35                  40                  45

Cys Asp Ala Cys Gly Met Gln Pro Ala Arg Thr Pro Gly Leu Ser Val
    50                  55                  60

```
<210> SEQ ID NO 46
<211> LENGTH: 66
<212> TYPE: PRT
<213> ORGANISM: Artificial Sequence
<220> FEATURE:
<223> OTHER INFORMATION: Description of Artificial Sequence: Human COMP
      domain
```

<400> SEQUENCE: 46

Gln Cys Gln Ser Pro Leu Gly Ser Asp Leu Gly Pro Gln Met Leu Arg
 1               5                  10                  15

Glu Leu Gln Gln Glu Thr Asn Ala Ala Leu Gln Asp Val Arg Asp Trp
            20                  25                  30

Leu Arg Gln Gln Val Arg Glu Ile Thr Phe Leu Lys Asn Thr Val Met
        35                  40                  45

```
Glu Cys Asp Ala Cys Gly Met Gln Gln Ser Val Arg Thr Gly Leu Pro
 50                  55                  60

Ser Val
 65
```

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 47
taatgcaggg tcagatccca ctgg                                          24

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 48
gtgggatctg accctgcatt aat                                           23

<210> SEQ ID NO 49
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 49
gtggtgacct ggctccgcag atgctgcgtg aactccagga aaccaacgct gctctc       56

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 50
gttggtttcc tggagttcac gcagcatctg cggagccagg tcaccaccca              50

<210> SEQ ID NO 51
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 51
caggacgtac gtgaactgct gcgtcagcag gttaaagaaa tcaccttcct gaaaaacac    59

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 52
gaaggtgatt tctttaacct gctgacgcag cagttcacgt acgtcctgga gagcagc        57

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 53
cgttatggaa tgcgatgcat gcggtatgca gccggctcgt accccggggc        50

<210> SEQ ID NO 54
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 54
tcagccccgg ggtacgagcc ggctgcatac cgcatgcatc gcattccata acgtgttttt        60
tcag        64

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 55
cgttatggaa gctgatgcag ctggtatgca gccggctcgt accccggggc        50

<210> SEQ ID NO 56
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 56
tcagccccgg ggtacgagcc ggctgcatac cagctgcatc agcttccata acgtgttttt        60
tcag        64

<210> SEQ ID NO 57
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 57
tgagcgttgg tggttctggt ggttctggtg gttctggtgg tgttctgtct cctgca        56

<210> SEQ ID NO 58
<211> LENGTH: 49
<212> TYPE: DNA
<213> ORGANISM: Artificial Sequence

```
<220> FEATURE:
<223> OTHER INFORMATION: Description of Artificial Sequence:
      Oligonucleotide Sequence for Comp cassette

<400> SEQUENCE: 58
ggagacagaa caccaccaga accaccagaa ccaccagaac caccaacgc              49

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 59
tgagcgttta ataatctaga taaggaggta aatatatgca cctgact                47

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 60
ccggagtcag gtgcatatat ttacctcctt atctagatta ttaaacgc               48

<210> SEQ ID NO 61
<211> LENGTH: 66
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 61
ctagtaaata ccgtggtggt tctggtggtt ctggtggttc tggtggtcag ggtcagatcc   60
cactgg                                                             66

<210> SEQ ID NO 62
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide Sequence for Comp cassette

<400> SEQUENCE: 62
gtgggatctg accctgacca ccagaaccac cagaaccacc agaaccacca cggtattta    59

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Linker
      between COMP domain and Dialpha globin

<400> SEQUENCE: 63

Gly Gly Ser Gly Gly Ser Gly Gly Ser Gly Gly
  1               5                  10

<210> SEQ ID NO 64
<211> LENGTH: 5
```

```
<212> TYPE: PRT
<213> ORGANISM: Artificial Sequence
<220> FEATURE:
<223> OTHER INFORMATION: Description of Artificial Sequence: Residues

<400> SEQUENCE: 64

Gly Gly Gly Lys Tyr
 1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence:N-terminus
      of the beta globin

<400> SEQUENCE: 65

Met His Leu Thr Pro Glu
 1               5

<210> SEQ ID NO 66
<211> LENGTH: 33
<212> TYPE: PRT
<213> ORGANISM: Artificial Sequence
<220> FEATURE:
<223> OTHER INFORMATION: Description of Artificial Sequence: Synthetic
      tetra ZIP GCN4 domain

<400> SEQUENCE: 66

Arg Leu Lys Gln Ile Glu Asp Lys Leu Glu Glu Ile Leu Ser Lys Leu
 1               5                  10                  15

Tyr His Ile Glu Asn Glu Leu Ala Arg Ile Lys Lys Leu Leu Gly Glu
                20                  25                  30

Arg

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: peptide
      linker

<400> SEQUENCE: 67

Gly Gly Ser Gly Gly Ser Gly Gly Ser Gly Gly
 1               5                  10

<210> SEQ ID NO 68
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 68
gggaagatag gatccactag tggtggctct ggcggctccg gtggctccgt gggccg          56

<210> SEQ ID NO 69
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide for tetra ZIP cassette
```

-continued

```
<400> SEQUENCE: 69
ttttgatttt aagcttctag acgttcaccc agcagttttt tgatacgagc cagttcgttt      60
tc                                                                    62

<210> SEQ ID NO 70
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 70
ggtggctccg tgggccgtct gaaacagatc gaagacaaac tggaagaaat cc              52

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 71
ttcgatctgt ttcagacggc ccacggagcc acc                                  33

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 72
tgtctaaact gtaccacatc gaaaacgaac tggctcgtat c                          41

<210> SEQ ID NO 73
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 73
gatacgagcc agttcgtttc cgatgtggta cagtttagac aggatttctt ccagtttgtc      60

<210> SEQ ID NO 74
<211> LENGTH: 61
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 74
gttattctat ggatccttaa ttaacgtctg aaacagatcg aagacaaact ggaagaaatc      60
c                                                                     61

<210> SEQ ID NO 75
<211> LENGTH: 62
<212> TYPE: DNA
<213> ORGANISM: Artificial Sequence
<220> FEATURE:
```

```
<223> OTHER INFORMATION: Description of Artificial Sequence:
      Oligonucleotide for tetra ZIP cassette

<400> SEQUENCE: 75
tttatttatt taagcttctg caggccaccg gagccaccgg agccgccaga gccaccacgt    60
tc                                                                  62

<210> SEQ ID NO 76
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 76
cgaagacaaa ctggaagaaa tcctgtctaa actgtaccac atcgaaaacg aactg         55

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 77
gtggtacagt ttagacagga tttcttccag tttgtcttcg                          40

<210> SEQ ID NO 78
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 78
gtccgtatca aaaactgct gggtgaacgt ggtggctctg gcg                       43

<210> SEQ ID NO 79
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide for tetra ZIP cassette

<400> SEQUENCE: 79
cgccagagcc accacgttca cccagcagtt ttttgatacg agccagttcg ttttcgat      58

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: WT leucine
      zipper

<400> SEQUENCE: 80

Met Lys Gln Leu Glu Asp Lys Val Glu Glu Leu Leu Ser Lys Asn Tyr
  1               5                  10                  15

His Leu Glu Asn Glu Val Ala Arg Leu Lys Lys Leu Val Gly Glu Arg
             20                  25                  30
```

```
<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence:peptide
      linker

<400> SEQUENCE: 81

Gly Gly Ser Gly Gly Ser Gly Gly Ser Gly Gly
 1               5                   10

<210> SEQ ID NO 82
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 82
actagtaaat accgtggtgg ttctggtggt tctggtggtt                               40

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 83
ctgtttcatt cgaccaccag aaccaccaga accaccagaa                               40

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 84
ctggtggtcg aatgaaacag ctggaagaca agttgaaga                                40

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 85
ggtagttttt agacagcagt tcttcaactt tgtcttccag                               40

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 86
actgctgtct aaaaactacc acctggaaaa cgaagttgct                               40
```

```
<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 87
ccaaccagtt ttttcagacg agcaacttcg ttttccaggt                          40

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 88
cgtctgaaaa aactggttgg tgaacgttaa tgatctagat                          40

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 89
gtgcatatat ttacctcctt atctagatca ttaacgttca                          40

<210> SEQ ID NO 90
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 90
cgcgcggatc cactagtaaa taacgtggtg gttctggtgg ttctggtgg                49

<210> SEQ ID NO 91
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide for leucine zipper cassette

<400> SEQUENCE: 91
cgcgtatata cgaagctttc tagattatta acgttcacca accagttttt tcag          54

<210> SEQ ID NO 92
<211> LENGTH: 53
<212> TYPE: PRT
<213> ORGANISM: Artificial Sequence
<220> FEATURE:
<223> OTHER INFORMATION: Description of Artificial Sequence: Arc Domain

<400> SEQUENCE: 92

Met Lys Gly Met Ser Lys Met Pro Gln Phe Asn Leu Arg Trp Pro Arg
 1               5                  10                  15

Glu Val Leu Asp Leu Val Arg Lys Val Ala Glu Glu Asn Gly Arg Ser
            20                  25                  30
```

Val Asn Ser Glu Ile Tyr Gln Arg Val Met Glu Ser Phe Lys Lys Glu
            35                  40                  45

Gly Arg Ile Gly Ala
    50

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: peptide
      linker

<400> SEQUENCE: 93

Gly Gly Ser Gly Gly Ser Gly Gly Ser Gly Gly
 1               5                  10

<210> SEQ ID NO 94
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 94
ctatttatat ttgaattcct gcaggccacc ggagccaccg gagccgccag                50

<210> SEQ ID NO 95
<211> LENGTH: 65
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 95
actaaataaa aaggatccac tagtggtggt tctggtggtt ctggtggttc tggtggtatg        60
aaagg                                                                    65

<210> SEQ ID NO 96
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 96
ggttctggtg gtatgaaagg aatgagcaaa atgccgcagt tcaatttgcg gtggcctaga        60
gaagtattgg                                                               70

<210> SEQ ID NO 97
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 97
gccaccgcaa attgaactgc ggcattttgc tcattccttt cataccacca gaacc             55

<210> SEQ ID NO 98

```
<211> LENGTH: 65
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 98
atttggtacg caaggtagcg gaagagaatg gtcggtctgt taattctgag atttatcagc    60
gagta                                                                65

<210> SEQ ID NO 99
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 99
agaattaaca gaccgaccat tctcttccgc taccttgcgt accaaatcca atacttctct    60
ag                                                                   62

<210> SEQ ID NO 100
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 100
ctggaaagct taagaagga agggcgcatt ggcgcgggtg gctctggcgg ctccggtggc     60

<210> SEQ ID NO 101
<211> LENGTH: 76
<212> TYPE: DNA
<213> ORGANISM: Artificial Sequence
<220> FEATURE:
<223> OTHER INFORMATION: Description of Artificial Sequence:
      Oligonucleotide for Arc cassette

<400> SEQUENCE: 101
gccaccggag ccgccagagc cacccgcgcc aatgcgccct tccttcttaa agctttccat    60
tactcgctga taaatc                                                    76

<210> SEQ ID NO 102
<211> LENGTH: 37
<212> TYPE: PRT
<213> ORGANISM: Artificial Sequence
<220> FEATURE:
<223> OTHER INFORMATION: Description of Artificial Sequence: peptide
      sequence of P22 Mut repressor oligomerizing domain

<400> SEQUENCE: 102

Ser Pro Val Thr Gly Tyr Arg Asn Asp Ala Glu Arg Leu Ala Asp Glu
 1               5                  10                  15

Gln Ser Glu Leu Val Lys Lys Met Val Phe Asp Thr Leu Lys Asp Leu
            20                  25                  30

Tyr Lys Lys Thr Thr
         35

<210> SEQ ID NO 103
<211> LENGTH: 11
```

```
<212> TYPE: PRT
<213> ORGANISM: Artificial Sequence
<220> FEATURE:
<223> OTHER INFORMATION: Description of Artificial Sequence: peptide
      linker

<400> SEQUENCE: 103

Gly Gly Ser Gly Gly Ser Gly Gly Ser Gly Gly
 1               5                   10

<210> SEQ ID NO 104
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 104
ggttctggtg gttctggtgg ttctggtggt tctccggtta ccggt              45

<210> SEQ ID NO 105
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 105
taccgtaacg acgatgaacg tctggctgac gaacagtctg aactg              45

<210> SEQ ID NO 106
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 106
attaggtggt cttcttgtac aggtctttca gggtgtcgaa aacca              45

<210> SEQ ID NO 107
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 107
tcttcttaac cagttcagac tgttcgtcag ccagacgttc agcgt              45

<210> SEQ ID NO 108
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 108
gttaagaaga tggttttcga caccctgaaa gacctgtaca agaagaccac ctaat         55

<210> SEQ ID NO 109
<211> LENGTH: 55
```

```
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 109
cgttacggta accggtaacc ggagaaccac cagaaccacc agaaccacca gaacc         55

<210> SEQ ID NO 110
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 110
cgcgcggatc cactagtaaa taccgtggtg gttctggtgg ttctggtgg               49

<210> SEQ ID NO 111
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 111
cgcgtatata cgaagctttc tagattatta ggtggtcttc ttgtacagg               49

<210> SEQ ID NO 112
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide for P22 domain cassette

<400> SEQUENCE: 112
ggaggttaat taatgcaggg tcagatccc                                     29

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide for Comp cassette

<400> SEQUENCE: 113
cgttggtttt atctgcagga gacagaacac c                                  31

<210> SEQ ID NO 114
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide for Comp cassette

<400> SEQUENCE: 114
gcggatccac tagtaaatac cgtggtggtt ctggtgg                            37

<210> SEQ ID NO 115
<211> LENGTH: 48
<212> TYPE: DNA
```

```
<213> ORGANISM: Artificial Sequence
<220> FEATURE:
<223> OTHER INFORMATION: Description of Artificial Sequence:
      Oligonucleotide for Comp cassette

<400> SEQUENCE: 115
gcgcgcgtat atacgaagct ttctagatta ttaaacgctc agccccgg                48

<210> SEQ ID NO 116
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide for Comp cassette

<400> SEQUENCE: 116
cgcgcggatc cactagtaaa taccgtggtg gttctggtgg ttctggtgg               49
```

GLOBINS CONTAINING BINDING DOMAINS

This application is the national stage of PCT/US96/20632, filed Dec. 20, 1996, which claims the benefit of U.S. Provisional Application Ser. No. 60/021,001, filed Dec. 22, 1995, now abandoned.

FIELD OF THE INVENTION

This invention generally relates to modified hemoglobins, and more particularly to globins containing non-naturally occurring binding domains.

BACKGROUND OF THE INVENTION

The oxygen carrying portion of red blood cells is the protein hemoglobin. Hemoglobin is a tetrameric molecule composed of two identical alpha globin subunits (alpha$_1$, alpha$_2$), two identical beta globin subunits (beta$_1$, beta$_2$) and four heme molecules, with one heme incorporated per globin. Heme is a large macrocyclic organic molecule containing an iron atom; each heme can combine reversibly with one ligand molecule such as oxygen. In a hemoglobin tetramer, each alpha subunit is associated with a beta subunit to form a stable alpha/beta dimer, two of which in turn associate to form the tetramer. The subunits are noncovalently associated through Van der Waals forces, hydrogen bonds and salt bridges.

Severe blood loss often requires replacement of the volume of lost blood as well as the oxygen carrying capacity of that blood. This replacement is typically accomplished by transfusing red blood cells (RBC's), either as packed RBC's or as units of whole blood. However, it is not always possible, practical or desirable to transfuse a patient with donated blood. Human blood transfusions are associated with many risks such as, for example, transmission of diseases and disease causing agents such as human immunodeficiency virus (HIV), non-A and non-B hepatitis, hepatitis B, *Yersinia enterocolitica*, cytomegalovirus, and human Tell leukemia virus. In addition, blood transfusions can be associated with immunologic reactions such as hemolytic transfusion reactions, imnmunosuppression, and graft versus host reactions. Moreover, blood must be typed and crossmatched prior to administration, and may not be available due to limited supplies.

When human blood is not available or the risk of transfusion is too great, plasma expanders can be administered. However, plasma expanders, such as colloid and crystalloid solutions, replace only blood volume, and not oxygen carrying capacity. In situations where blood is not available for transfusion, a red blood cell substitute that can transport oxygen in addition to providing volume replacement is desirable. Solutions of cell-free hemoglobin can increase and/or maintain plasma volume and decrease blood viscosity in the same manner as conventional plasma expanders, but, in addition, a hemoglobin-based red blood cell substitute can support adequate transport of oxygen from the lungs to peripheral tissues. Moreover, an oxygen-transporting hemoglobin-based solution can be used in most situations where red blood cells are currently utilized. For example, oxygen-transporting hemoglobin-based solutions can be used to temporarily augment oxygen delivery during or after pre-Aonation of autologous blood prior to the return of the autologous blood to the patient.

To address this need, a number of red blood cell substitutes have been developed (Winslow, R. M. (1992) *Hemoglobin-based Red Cell Substitutes*, The Johns Hopkins University Press, Baltimore 242 pp). These substitutes include synthetic perfluorocarbon solutions, (Long, D. M. European Patent 0307087), stroma-free hemoglobin solutions derived from a variety of mammalian red blood cells which may or may not be chemically crosslinked (Rausch, C. and Feola, M., U.S. Pat. Nos. 5,084,558 and 5,296,465; Sehgal, L. R., U.S. Pat. Nos. 4,826,811 and 5,194,590; Vlahakes, G. J. et al., (1990) *J. Thorac. Cardiovas. Surg.* 100: 379–388) and hemoglobins expressed in and purified from genetically engineered organisms (for example, non-erythrocyte cells such as bacteria and yeast, Hoffman et al., WO 90/13645; bacteria, Fronticelli, C. et al., U.S. Pat. No. 5,239,061; yeast, De Angelo et al., WO 93/08831 and WO 91/16349; and transgenic mammals, Logan et al., WO 92/22646; Townes, T. M and McCune, S. L., WO 92/11283). These red blood cell substitutes have been designed to replace or augment the volume and the oxygen carrying capability of red blood cells.

However, red blood cell replacement solutions that have been administered to animals and humans have exhibited certain adverse events upon administration. These adverse reactions have included hypertension, renal failure, neurotoxicity, and liver toxicity (Winslow, R. M., (1992) *Hemoglobin-based Red Cell Substitutes*, The Johns Hopkins University Press, Baltimore 242 pp.; Biro, G. P. et al., (1992) *Biomat., Art. Cells & Immob. Biotech.* 20: 1013–1020). In the case of perfluorocarbons, hypertension, activation of the reticulo-endothelial system, and complement activation have been observed (Reichelt, H. et al., (1992) in *Blood Substitutes and Oxygen Carriers*, T. M. Chang (ed.), pg. 769–772; Bentley, P. K. supra, pp. 778–781). For hemoglobin based oxygen carriers, renal failure and renal toxicity is the result of the formation of hemoglobin alpha/beta dimers. The formation of dimers can be prevented by chemically crosslinking (Sehgal, et al., U.S. Pat. Nos. 4,826,811 and 5,194,590; Walder, J. A. U.S. Reissue Pat. No. RE34271) or genetically linking (Hoffman, et al., WO 90/13645) the hemoglobin dimers so that the tetramer is prevented from dissociating.

Prevention of dimer formation has not alleviated all of the adverse events associated with hemoglobin administration. Blood pressure changes and gastrointestinal effects upon administration of hemoglobin solutions have been attributed to vasoconstriction resulting from the binding of endothelium derived relaxing factor (EDRF) by hemoglobin (Spahn, D. R. et al., (1994) *Anesth. Analg.* 78: 1000–1021; Biro, G. P., (1992) *Biomat., Art. Cells & Immob. Biotech.*, 20: 1013–1020; Vandegriff, K. D. (1992) *Biotechnology and Genetic Engineering Reviews*, Volume 10: 4044493 M. P. Tombs, Editor, Intercept Ltd., Andover, England). Endothelium derived relaxing factor has been identified as nitric oxide (NO) (Moncada, S. et al., (1991) *Pharmacol. Rev.* 43: 109–142 for review); both inducible and constitutive NO are primarily produced in the endothelium of the vasculature and act as local modulators of vascular tone.

Some inflammatory responses are also mediated by nitric oxide (Vandegriff, (1992) *Biotechnology and Genetic Engineering Reviews*, Volume 10: 404 453 M. P. Tombs, Editor, Intercept Ltd., Andover, England; Moncada, S., et al., supra.). For example, nitric oxide produced by the endothelium inhibits platelet aggregation and as nitric oxide is bound by cell-free hemoglobin -solutions, platelet aggregation may be increased. As platelets aggregate, they release potent vasoconstrictor compounds such as thromboxane A$_2$ and serotonin (Shuman, M. (1992) in *Cecil Textbook of Medicine*, J.B. Wyngaarden, L. H. Smith and J. C. Bennett, ed., W. B. Saunders Co, Philadelphia, pages 987–992). These may act synergistically with the reduced nitric oxide levels due to binding by hemoglobin to result in an exaggerated vasoconstriction.

In addition to modulating platelet aggregation, nitric oxide inhibits neutrophil attachment to cell walls. Increased adhesion of neutrophils to cell walls may lead to cell wall damage. Endothelial cell wall damage in rabbits has been observed upon infusion of some hemoglobin solutions; this kind of damage is consistent with uptake of endogenous nitric oxide by hemoglobin (White, et al., (1986) *J. Lab. Clin. Med.* 108: 121–131; Vandogriff (1992) *Biotechnology and Genetic Engineering Reviews*, Volume 10: 404453 M. P. Tombs, Editor, Intercept Ltd., Andover, England). In all these cases, a hemoglobin molecule with reduced scavenging of nitric oxide and with a physiologically acceptable oxygen affinity might ameliorate some of these possible effects while still functioning as an effective oxygen carrier.

When hemoglobin is contained in red blood cells, it cannot move beyond the boundaries of blood vessels. Therefore, nitric oxide must diffuse to the hemoglobin in an RBC before it is bound. When hemoglobin is not contained within an RBC, such as is the case with hemoglobin based blood substitutes, it may pass beyond the endothelium lining the blood vessels and penetrate to the extravascular space (extravasation). Thus a possible mechanism of advere events associated with administration of extracellular hemoglobin may be excessive inactivation of nitric oxide by hemoglobin that has entered the extravascular space of blood vessels. NO is constitutively synthesized by the vascular endothelium. Rapid inactivation of NO in the endothelium and extravascular space may lead to vasoconstriction and the pressor response observed after infusions of cell-free hemoglobin. Larger hemoglobins, i.e. polymers of hemoglobin tetramers, may result in reduced extravasation because of their increased size. Reduced extravasation may, in turn, lead to reduced pressor effects resulting from infused hemoglobin solutions.

Larger hemoglobins may also have improved half-life characteristics. Larger molecules are generally associated with significantly longer serum half-life when administered in vivo. Indeed, larger hemoglobins have been sought by chemical polymerization. For example, U.S. Pat. No. 4,001,401, U.S. Pat. No. 4,001,200, U.S. Pat. No. 4,336,248 and U.S. Pat. No. 4,053,590 all relate to polymerization of red blood cell-derived hemoglobin by chemical crosslinking to achieve hemoglobins with higher molecular weights. The results of tie crosslinking reactions are generally polydisperse compositions of covalently cross-linked aggregates. Bucci, U.S. Pat. No. 4,584,130, at col. 2, comments that "the polyhemoglobin reaction products are a heterogeneous mixture of various molecular species which differ in size and shape. The molecular weights of these polyhemoglobins range from 64,500 to 600,000 Daltons. The separation of individual molecular species from the heterogeneous mixture is virtually impossible. In addition(although longer retention times in vivo are obtained using polyhemoglobins, the oxygen affinity thereof is higher than that of stroma-free hemoglobin." Furthermore, according to Tye, U.S. Pat. No. 4,529,719, polymerized pyridoxylated hemoglobin has "a profound chemical heterogeneity malting it difficult to study as a pharmaceutical agent."

Thus it is well recognized that random polymerization is difficult to control and that a heterogeneous mixture of different polymers can be obtained. Moreover, treatment of hemoglobin with polymerizing reagents is cumbersome and increases the cost of the product by increasing the material costs and increasing the number of production and purification steps.

In addition to polymerization by chemical means, genetic engineering techniques can be used to link proteins. Anderson et al., WO 93/09143 disclose the polymerization of hemoglobin tetramers by means of cysteine mutations introduced into one or more of the globin subunits that then allow the formation of disulfide bonds. However, these disulfide bonds may be cleaved in vivo, leading to reduction of molecular weight and reduced half-life. Alternatively, formation of these disulfide linkages may require the addition of exogenous chemical reagents, with the attendant disadvantages of exogenous chemical reagents discussed above.

In addition to mutations of residues to provide cysteines for the formation of disulfide, proteins can be linked by direct genetic fusion. These linkers can encode peptides linkers having unique characteristics. See, e.g., Rutter, U.S. Pat. No. 4,769,326. Linking of the genes can be done by fusion of the genes that code for the proteins of interest by removing the stop codon of the first gene and joining it in phase to the second gene. Parts of genes may also be fused, and spacer DNA's which maintain phase may be interposed between the fused sequences. The product of a fused gene is a singe fusion polypeptide.

Hoffman, et al., WO88/09179 describes the production of globin domains fused to leader peptides which are cleaved prior to processing the final product. Anderson et al., WO 93/09143 describe the production, in bacteria and yeast, of hemoglobin and analogs thereof. They disclosed analogs of hemoglobin proteins in which one of the component polypeptide chains consists of two alpha or two beta globin amino acid sequences covalently connected by peptide bonds, preferably through an intermediate linker of one or more amino acids, without branching.

In addition to chemically produced and genetically linked polymeric hemoglobins, naturally occurring polymeric hemoglobins have been reported in various vertebrates and invertebrates. Murine polymeric hemoglobins are described in Bonaventura & Riggs, *Science,* 149:800–802 (1967); and Riggs, *Science,* 147:621–623 (1965). A polymerizing monkey hemoglobin variant is reported in Takenaka et al., *Biochem. Biophys. Acta,* 492:433444 (1977); Ishimoto et al., *J. Anthrop. Soc. Nippon,* 83(3):233–243 (1975). Both amphibians and reptiles also possess polymerizing hemoglobins. Tam et al., *J. Biol. Chem.,* 261:8290–94 (1986). These hemoglobins polymerize as a result of formation of disulfide bonds between two or more subunits or tetramers.

Larger hemoglobins can also result from the interaction of more than four globin subunits to form a multimeric hemoglobin. For example, the extracellular hemoglobin of the earthworm (*Lumbricus terrestris*) has twelve subunits, each being a dimer of structure $(abcd)_2$ where "a", "b", "c", and "d" denote the major heme containing chains. The "a", "b", and "c" chains form a disulfide-linked trimer. The whole molecule is composed of 192 heme-containing chains and 12 non-heme chains, and has a molecular weight of 3800 kDa. Other invertebrate hemoglobins are also large multi-subunit proteins. For example, the brine shrimp Artemia produces three polymeric hemoglobins with nine genetically fused robin subunits (Manning, et al., (1990) Nature, 348.–6S3). These are formed by variable association of two different subunit types, a and b. Of the eight intersubunit linkers, six are 12 residues long, one is 11 residues and one is 14 residues, Three human mutants are known that polymerize as a result of formation of intermolecular (first tetramer to second tetramer) disulfide bridges. Tondo, *Biochem. Biophys. Acta,* 342:15–20 (1974) and Tondo, *An. Acad. Bras. Cr.,*

59:243–251 (1987) describe one sudi mutant known as Hb Porto Alegre. Hb Mississippi is characterized by a cysteine substitution in place of Ser CD3(44)beta and is believed to be composed of ten or more hemoglobin tetramers according to Adams et al., *Hemoglobin*, 11(5):435–542 (1987). Hemoglobin Ta Li is characterized by a beta83(EF7)Gly→Cys mutation, which showed slow mobility in starch gel electrophoresis, indicating that it too was a polymer. However, all of the naturally occurring polymerizing hemoglobins discussed above, whether of human or non-human origin, have oxygen affinities that may render them unsuitable for use as blood substitutes. In addition, these naturally occurring polymerizing hemoglobins may be difficult to collect in the quantities required to be a useful blood substitute, or they may elicit immunogenic response when administered intravenously.

Many proteins, including hemoglobin, are known to exist as oligomers (diners, trimers, tetramerc et.), and in several cases a discrete folding unit (or "domain") within an oligomeric protein is responsible for the assembly of the oligomer (Landschultz, Johnson and McKnight, *Science*, 240, 1759, (1988); McWhirter, Galasso and Wang, *Mol. Cell. Biol.*, 13, 7587, (1993); Stuirzbecher et al., *Oncogene*, 7, 1513, (1992); Morgelin et. al., *J. Biol. Chem.*, 267, 6137, (1992)). The ability of these domains to promote oligomerization has been demonstrated by chemical synthesis or bacterial expression of polypeptides with sequences corresponding to putative oligomerizing domains and subsequent characterization (O'Shea, Rutkowski, Stafford and Kim, *Science*, 245, 646, (1989); O'Neil, Hoess and DeGrado, *Science*, 249, 774, (1990); Anthony-Cahill et al., *Science*, 255, 979, (1992); Pavletich, Chambers and Pabo, *Genes Dev.*, 7, 2556, (1993); Efimov, Lustig, and Engel, *FEBS Letters*, 341, 54, (1994)). It has been shown that the oligomerizing domain from the human tumor suppressor p53 protein can be replaced by the dimerizing domain from yeast transcription factor GCN4. The resultant chimeric protein possessed activity sufficient to suppress tumor growth in cultured cells (Pietenpol et al., *Proc. Nat'l Acad. Sci. USA*, 91, 1998, (1994)). Fusion of the GCN4 sequence to the DNA-binding domain of bacteriophage lambda repressor yields a stable, biologically active dimer (Hu, O'Shea, Kim and Sauer, *Science*, 250, 1400, (1990)). The genetic fusion of the GCN4 dimerizing domain to single-chain antibody $F_v$ genes yields a "miniantibody" that is a dimer (Pack and Plückthun, *Biochemistry*, 31, 1579, (1992)). These oligomers are non-covalently assembled and form spontaneously without the addition of exogenous chemical covalent crosslinking agents. However, oligomerizing domains have not been fused to globins.

Thus, a need exists for methods for producing larger hemoglobins that can be assembled without the addition of exogenous chemical crosslinking agents, wherein the size of the final multimeric hemoglobin can be constrained if desired. Such larger hemoglobins may reduce extravasation and increase halflife. The present invention satisfies this need and provides related advantages.

SUMMARY OF THE INVENTION

This invention relates to globins containing non-naturally occurring binding domains. These binding domains are fused either directly or through a linker to the N terminus or the C ternminu, or both of any of the globin domains composing the hemoglobin, or alternatively, these binding domains can replace or augment existing or engineered regions of the globin. The globins domains can be individual globin domains, or they may be globin domains that have been joined by means of a peptide linker.

In one aspect of the invention, these binding domains bind to non-peptide ligands, for example biotin. In another aspect of the invention, the binding domain is an oligomerizing domain from any naturally occurring or artificial oligomer. Preferably, the oligomerizing domain is the oligomerizing domain from a naturally occurring oligomer, for example the oligomerizing domain from p53, COMP, arc, Mnt, BMP, BRS, Urechis or GCN4.

This invention also relates to multimeric hemoglobins comprised of at least one globin containing one or more non-naturally occurring binding domains. Thus, the present invention further relates to hemoglobins composed of more than four globins.

This invention also relates to nucleic add molecules having a nucleic acid sequence encoding such globins containing non-naturally occurring binding domains. In one embodiment, the nucleic add molecule encodes a &Iobin containing the p53 oligomerizing domain. In a further embodiment, the nucleic add molecules encodes a globin containing the COMP oligomerizing domain. In a still further embodiment, the nucleic add molecules encode a globin containing the GCN4 oligomerizing domain. In another embodiment, the nucleic acid molecule encodes a globin containing the avidin binding domain for biotin.

Methods for making globins containing non-naturally occurring binding domains as well as multimeric hemoglobins comprising at least one globin containing a non-naturally occurring binding domain are also provided by the instant invention.

DETAILED DESCRIPTION OF THE INVENTION

The present invention generally relates to globin proteins containing one or more non-naturally occuring binding domains. The term globin is intended to embrace all proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are therefore embraced by the term globin. For example, the subunits of bovine hemoglobin are within the scope of this term. Thus, the term "alpha globin" is intended to include but not be limited to naturally occurring alpha globins, including normal human alpha globin, and mutants thereof. A "beta globin" is analogously defined. Therefore, according to the present invention, a polypeptide can be considered a globin if it has a greater sequence identity with a naturally occurring globin than would be expected from chance and also has the characteristic higher structure (e.g., the "myoglobin fold") generally associated with globins. In many vertebrates and some invertebrates, these four globins associate non-covalently to form a hemoglobin tetramer.

Without departing from the scope of the invention, mutations of the globins can be introduced to alter, for example, (1) oxygen affinity, cooperativity, or stability, (2) to facilitate genetic fusion or crosslinking, or (3) to increase the ease of expression and assembly of the individual chains. Guidance as to certain types of mutations is provided, for example, in U.S. Pat. No. 5,028,588 and PCT Publication No. WO 93/09143, both incorporated herein by reference. In addition, the present invention is further directed to the addition of oligomerizing domains to globins that have been already genetically fused. Such genetically fused globins are provided, for example, in PCT publication No. WO 90/13645, herein incorporated by reference. These genetically fused globins include, for example, di-alpha globin (two alpha globins used by a glycine linker between the N terminus of one alpha globin and the C terminus of a second alpha globin) and di-di-alpha globins (two di-alpha globins further fused by the insertion of a linker between the N and C termini of the di-alpha globins). The present invention further includes molecules which depart from those taught herein by gratuitous mutations that do not substantially affect biological activity.

The present invention is directed to globins containing binding domains that do not occur naturally in the globin (non-naturally occurring binding domains). Accordingly, the term "non-naturally occurring" refers to whether or not a particular binding domain is naturally found in the globin of interest, and not to the source of the binding domain. Thus, the binding domain can be, for example, a naturally-occurring binding domain, a mutant of a naturally-occurring binding domain or a synthetic binding domain. Moreover, a binding domain that is found naturally within a given globin, but that has been moved within the globin to a location not found in nature, or that has been added to the globin is also a "non-naturally occurring binding domain." This invention is therefore directed to, for example, an alpha globin containing more beta globin binding domains than occur in nature, or a beta globin linked to, for example, the p53 binding domain.

A binding domain of the present invention is a peptide sequence which will spontaneously associate, primarily through non-covalent interactions, with a ligand or another peptide sequence and is capable of forming oligomers. The non-covalently associated complex (or oligomer) can be further stabilized by the addition of, for example, cysteine residues, that may form disulfides after the peptides or peptides and ligands bind. An oligomerizing domain is a specialized binding domain that is defined as a peptide sequence which will associate specifically with other peptide domains, which may be the same or different. For example, one coiled-coil helix can associate with one or more similar helices to form dimers or higher order oligomers where the oligomer core is made up of identical coiled-coil helices. Alternatively, a peptide binding domain can bind to a very different peptide binding domain on a different molecule. For example, fusion of an alpha globin to each end of dialpha globin can produce a trimeric hemoglobin in the presence of beta globins as alpha globins oligomerize with other alpha globins (like oligomerizing domains) and beta globins (unlike oligomerizing domains). In other words, the additional alpha globins on the two oligomerized dialpha globins assemble with each other and beta globins to form two normal hemoglobin teframers that are linked to a new central hemoglobin. This interaction may be further stabilized by the incorporation of cys mutations in the central hemoglobin as taught in U.S. Pat. No. 5, 449,759, herein incorporated by reference. Similarly, the added binding domain can be from the globin binding domain from another species, for example, the globin domain can be from Urechis hemoglobin (Kolatkar and Hackert, *J. Mol. Biol.*, 237: 87–97 (1994). This is a hemoglobin composed of four identical subunits. A fusion of di-alpha globin the Urechis globin would lead to the formation of a tetrameric multimeric hemoglobin, for example.

An oligomerizing domain is different from a "ligand binding domain" in that a ligand binding domain will not necessarily associate with itself to form oligomers but can effect oligomerization by binding to a non-peptide ligand (note, however, that streptavidin would be an example of a ligand binding domain that can self-associate; streptavidin itself forms a tetramer, but also binds to biotin). Thus, a ligand binding domain can be added to a globin molecule. When the globin molecule is then exposed to an appropriate polyfunctional ligand, such as for example a dendrimer with multiple biotin moieties, the system will form oligomers. Alternatively, a ligand binding domain that is naturally biotinylated can be added to a globin; in the presence of streptavidin, a tetrameric hemoglobin can be formed.

The binding domain can be a naturally occurring peptide sequence or a non-naturally occurring peptide sequence. Where a discrete binding domain is known, this domain can be linked to the globin. In those cases where a protein exists as an oligomer but no discrete domain is responsible for the oligomerization (i.e. the amino acid residues defining the protein oligomer interface span one or more regions or domains in the protein), the entire sequence of the oligomeric protein (or the desired portion of the sequence) can be linked, by any suitable means, to the globin in order to generate the desired oligomer. These sequences, and the globins themselves, can be expressed in any suitable biological expression system, as further described below, or they can be synthesized by any appropriate chemical means, such as by solid or solution phase peptide synthesis.

The extent of oligomerization can be controlled by the selection and placement of the binding domain. For example, a dimeric globin can be created when a binding domain that is known to form dimers is linked to, for example, an alpha globin. When then two alpha globins interact, a dimeric alpha globin is assembled. That is, two alpha globins are linked through the non-naturally occurring dimerizing domain that has been added to each of the alpha globins. In the same manner, a trimeric globin oligomer can be formed if the oligomerizing domain is a trimerizing domain, a tetrameric globin oligomer can be formed if the oligomerizing domain is a tetramerizing domain, and so on. Note, polymers of the globin can be formed if the domain is a polymerizing domain.

Accordingly, multimeric hemoglobins can be formed if an oligomerizing domain is linked to one or more globins comprising genetically linked globins, for example, di-alpha globin. For example, when an oligomerizing domain is linked to the N terminus of for example, alpha globin as described above, or di-alpha globin, the corresponding oligomeric di-alpha is formed. That is, the di-alpha globins are non-covalently linked through the interaction of the oligomerizing domain. Of course, various moieties that form covalent bonds could be introduced into the oligomer to further stabilize the interaction. If the oligomeric di-alpha globin is assembled in the presence of beta globin, the corresponding oligomeric hemoglobin results because beta globin will associate spontaneously with alpha globin, so long as the beta globin binding domains in the alpha globin are available for binding to the beta globins.

A polymeric hemoglobin can form when linkage of the binding domain is to a single alpha globin. That is, each alpha globin can have an oligomerizing domain that binds to a corresponding oligomerizing domain on another alpha globin. Each of these alpha globins is capable of associating with another alpha globin in the presence of beta globins to form a tetrameric hemoglobin. The binding domains on the added alpha globins then continue to oligomerize to form polymeric hemoglobin. Note that all these changes to the alpha globin may be done in any globin, for example, beta globin. Multimeric hemoglobin would then form by oligomerization of the beta globins, and assembly with alpha globins.

The dimerizing domain from yeast GCN4 protein is particularly suited for generation of dimeric hemoglobin multimers by the methods described herein. The GCN4 dimerizing domain is a single a-helix which pairs with its partner to form a parallel coiled-coil (O'Shea, Rutkowski, Stafford and Kim, *Science,* 245, 646, (1989)). The X-ray crystal structure of the GCN4 coiled-coil has been determined (O'Shea, Klemm, Kim and Alber, *Science,* 254, 539, (1991)), and factors affecting stability and oligomerization state of native and mutant GCN4 coiled-coil peptides have been determined (Harbury, Zhang, Kim and Alber, *Science,* 262, 1401, (1993); O'Neil, Hoess and DeGrado, *Science,* 249, 774, (1990)). When used in this application, "GCN4 derivatives" refers to both artificial and naturally occurring mutants of the GCN4 domain. In addition, several model coiled-coil peptides have been extensively studied and rules governing stability of these designed peptides have been reported (Hodges, Zhou, Kay and Semchuk, *Peptide Res.,* 3, 123, (1990); Zhu et al., *Int. J. Peptide Protein Res.,* 40, 171, (1992); Lumb and Kim, Biochemistry, 34, 8642, (1995)). Another useful dimerizing binding domain is the binding domain from the Arc repressor of bacteriophage P22 (Schildbach, J F, Milla M E, Jeffrey PD, Raumann BE, Sauer RT (1995). Biochemistry 34: 13914–19). Arc repressor is a dimeric polypepfide of 53 amino acids.

Alternatively, a small tetramerizing sequence such as the C-terminal tetramerizing domain from the tumor suppressor p53 can be fused to the globin of interest. The structure of this domain has been determined from the crystal Jeffrey, Gorina and Pavletich, Science, 267, 1498, (1995)) and in solution (Clore et al., Nature Struct. Biol., 2, 321, (1995)). In vitro binding studies show that a protein fragment comprising 53 amino acids is sufficient to promote tetramerization (Pavletich, Chambers and Pabo, Genes Dev., 7, 2556, (1993)). Another tetrameric binding domain suitable for this invention is the Mnt repressor of bacteriophage P22 (Waldburger, C. D. and R. T. Sauer (1995). Biochemistry 34(40): 13109–13116). Mnt repressor is a tetrameric polypeptide of 82 amino acids. Additional tetramerizing binding domains suitable for this invention are streptavidin and avidin. Streptavidin (Argarana, C., Kuntz, I.D., Birken, S, Axel, R. and Cantor, C. R. (1986) Nucleic Acids Res. 14:1871) and avidin (Green, N. M. (1975) Adv. Protein Chem. 29:85) are homologous tetrameric polypeptides of approximately 125–127 and 128 amino adds, respectively.

Another suitable tetramerizing binding domain is the recognition site for biotin ligase (BLS). BLS polypeptide sequences have been described for various proteins: for example, the C-terminal 87 residues of the biotin carboxy carrier protein of *Escherichia coli* acetyl-CoA carboxylase (Chapman-Smith, A., D. L. Turner, et al. (1994). Biochem J. 302: 881–7); the C-terminal 67 residues of carboxyl-terminal fragments of human propionyl-CoA carboxylase alpha subunit may be used (Leon-Del-Rio, A. and R. A. Gravel (1994) J. Biol. Chem. 269(37): 22964–8); and residues 18–123 of *Propionibacterium freudenreichii* transcarboxylase 1.3S biotin subunit (Yamano, N., Y. Kawata, et al. (1992) Biosci. Biotechnol. Biochem. 56(7): 1017–1026). Globin proteins fused to a BLS can be biotinylated either in vitro, or in vivo by biotin ligase. Biotinylated globins then interact specifically with tetrameric avidin or streptavidin to form a tetrameric globin derivative.

Peptide mimetics of the biotin molecule described above can also be utilized in the instant invention. Peptide sequences have been described which confer the ability to bind directly to streptavidin without the presence of biotin. Such a biotin mimetic peptides ("BMP") have been described, for example, by Schmidt and Skerra (Schmidt, T. G. M. and A. Skerra (1993). Protein Eng 6(1): 109–122) and Weber et al. (Weber, P. C., Pantoliano, M. W., Thompson, L. D. (1992) Biochemistry 31:9350–9354.). Globin fused to a BMP interacts specifically with tetrameric avidin or streptavidin to form a tetrameric globin.

Globins can also be fused to a short peptidic binding domain ("BBD") which confers affinity for biotin. The peptide sequences that bind biotin have been described (Saggio, I. and Laufer, R. (1993) Biochem. J. 293:613–616). The globin-BBD fusion protein is reacted with an oligomeric array of 2–6 biotin molecules covalently linked to a dendrimer molecule. Such dendrimer molecules have been described by Mekelberger and Vogtle (Mekelberger, B. and Vogtle, F. Angewante Chemie, International edition in English, 31(12):1571–1576).

A pentameric globin can be created by linkage of, for example, the pentamerization domain from Cartilage Oligomeric Matrix Protein (COMP) to the N-terminus of a dialpha globin. Efimov et. al. (referenced above) report that a protein fragment of COMP comprising residues 2083 expressed in *E. coli* was shown by electron microscopy to form cylindrical structures similar to the corresponding segment in the intact native COMP protein. The cylindrical structures were comprised of five covalently linked peptide chains; the covalent linkage is believed to be mediated by two cysteine residues, Cys-68 and Cys-71 (Oldberg et. al., *J. Biol. Chem.,* 267, 22346 (1992)). Efimov et. al. reported that both the oxidized and reduced recombinant peptides had circular dichroism spectra characteristic of an a-helical structure. Because disulfide bond formation between Cys-68 and Cys-71 is only consistent with a parallel arrangement of five chains, the authors suggested that the assembly domain of COMP consists mainly of five parallel a-helices assembled in a bundle. Native PAGE and sedimentation velocity experiments suggested that both reduced and oxidized peptides have the same pentameric structure (Efimov et. al., cited above). The fact that reduced peptides apparently associate to form pentamers suggests that the cysteines are not required for oligomerization.

The non-naturally occurring binding domain can be inserted anywhere in the globin molecule so long as the desired biological activity of the globin is not substantially affected. For example, the non-naturally occurring binding domain can be added to either the N terminus or the C terminus of the globin of interest. Particularly suitable globins for these kind of additions are di-alpha globin or di-di-alpha globin. The oligomerizing domain can be added, for example, directly or through any suitable linker sequence to the N or C terminus. Such linkers can be derived from mouse IgG3 hinge regions (Pack and Plückthun, supra), or human IgAl hinge regions (Hallewell et al., *J. Biol. Chem.,* 264, 5260, (1989)). For example, simple repeats of one or a few amino acids can also be used as linkers. Argos reported that Thr, Ser, Gly and Ala are the most desirable constituent amino acids for a linker based on results of a survey of linker regions listed in the Brookhaven protein database (Argos, *J. Mol. Biol.,* 211, 943, (1990)). Particularly suitable linkers are linkers based on GlyGlyGlyGlySer (SEQ. ID. NO. 1) repeats (Holliger, Prospero and Winter, *Proc. Nat'l Acad. Sci USA,* 90, 6444, (1993), and GlyGlyGlySer (SEQ. ID. NO. 2) repeats (Neuhold and Wold, Cell, 74, 1033, (1993).

In addition, non-naturally occurring binding domains can be placed within the globin itself. For example, the D helix of beta globin is known to have little effect on the oxygen binding characteristics of the globin, and therefore is a good candidate location for placement of a non-naturally occurring binding domain, either by insertion within the D-helix or replacement of part or all of the D-helix itself. Other globins do not have the D-helix region, but a binding domain may be placed in an equivalent region (Komiyama, N., Shih, D., Looker, D., Tame, J., and Nagai, K., *Nature*, 352, 349–351, (1991)). Alternatively, a non-naturally occurring binding domain can be inserted as a new helical or non-helical region in the globin. Such regions can be readily determined by one of skill in the art using the guidance presented herein.

The invention further provides nucleic acids encoding the novel globins, of the present invention. Those skilled in the art can readily derive a desired nucleotide sequence based on the knowledge of published nucleotide or amino acid sequences of known hemoglobin subunits, linkers and binding domains with selection of codons and control elements specific for the organism used for expression, using methods known in the art. For example, the amino acid sequence of the di-alpha domain and the beta domain of a synthetic hemoglobin can be used to derive the nucleic acids of the present invention, both of which are identified in FIG. 12 of PCT Publication WO 90/13645, incorporated herein by reference, with the following corrections to the nucleotide sequence: bases 55, 56 and 57 (codon 19) should read GCG and bases 208 and 209 (the first two bases of codon 70) should read GC. The following changes to the amino acid sequence of this figure would yield the pseudotetramer, rHb1.1: the Gly-Gly bridge at residues 142 and 143 of the di-alpha domain can be changed to a single Gly residue bridging alpha$_1$ and alpha$_2$ domains; residues 54 and 97 of the di-alpha domain should read Gln; residue 70 of the beta subunit should read Asn; and residue 107 of the beta subunit should read Lys. The pseudotetramer rHb1.1 is also described in Looker et al., *Nature*, 356:258–260 (1992), incorporated herein by reference. This pseudotetramer is composed of two alpha globin domains joined by a peptide linker to form di-alpha globin and two non-fused beta globins. A similar pseudotetramer can be composed of genetically fused di-beta globins assembled with alpha globins.

The nucleic adds of the present invention can be used to construct plasmids to be inserted into appropriate recombinant host cells according to conventional methods or as described in the Examples below. Any suitable host cell can be used to express the novel polypeptides. Suitable host cells include, for example, bacterial, yeast, mammalian and insect cells. *E. coli* cells are particularly useful for expressing the novel polypeptides. Preferably, when multiple subunits are expressed in bacteria, it is desirable, but not required, that the subunits be co-expressed in the same cell polycistronically as described in WO 93/09143. The use of a single promoter is preferable, but not required, in *E. coli* to drive the expression of the genes encoding the desired proteins.

The present invention is also directed to novel hemoglobins comprised of at least one globin containing a non-naturally occurring binding domain. Generally, hemoglobins comprised of the globins of the present invention will form multimeric hemoglobins, that is hemoglobins comprising four or more globins or globin domains. Such multimeric hemoglobins include dimeric hemoglobins (two tetrameric or pseudotetrameric hemoglobins combined through a dimerizing binding domain), trimeric hemoglobins (three tetrameric or pseudotetrameric hemoglobins) and higher order multimers or polymeric hemoglobins. However, according to the present invention, the term multimeric hemoglobins also includes multimeric hemoglobins that are comprised of a single type of globin, for example, multimeric hemoglobin comprised only of alpha subunits, as well as tetrameric hemoglobins that are not oligomerized, but that contain at least one globin containing a non-naturally occurring binding domain.

The novel multimeric hemoglobins of the present invention are formed because of the association of new binding domains that are introduced by genetic engineering techniques into the sequence of the original globin molecules comprising the multimeric hemoglobin. Note that generally, alpha globin associates readily and very strongly with beta globin to form an alpha/beta dimer. For example, beta globins associate with alpha globins spontaneously and essentially irreversibily. Thus, when genetically fused alpha globins (di-alpha) are expressed along with beta globin, recombinant fused hemoglobin (rHb 1.1, described in WO 90/13645) is formed. That is, the alpha globins are genetically fused, and these alpha globins spontaneously oligomerize with beta globin through naturally occurring binding domains. The introduction of additional oligomerizing domains, as taught herein, can therefore result in the formation of higher order multimeric hemoglobins.

The multimeric hemoglobins of the instant invention can be purified by any suitable purification method known to those skilled in the art. Useful purification methods for the hemoglobins of the present invention are taught in PCT Publication WO 95/14038, incorporated herein by reference. Briefly, the methods described therein involve an immobilized metal affinity chromatography resin charged with a divalent metal ion such as zinc, followed by a Q-SEPHAROSE anion exchange column. According to this publication, the solution containing the desired Hb-containing material to be purified can first be heat treated to remove protoporphyrin IX-containing Hb. This basic purification method can be further followed by a sizing column (S-200), then another anion exchange column. The resulting solution can then be buffer exchanged into the desired formulation buffer. Other suitable techniques using anion and cation exchange chromatography techniques are described in PCT publication number WO 90/13645.

The multimeric hemoglobins of the present invention can be used for formulations useful for in vitro or in vivo applications. Such in vitro applications include, for example, the delivery of oxygen by multimeric hemoglobins of the instant invention for the enhancement of cell growth in cell culture by maintaining oxygen levels in vitro (DiSorbo and Reeves, PCT publication WO 94/22482, herein incorporated by reference). Moreover, the multimeric hemoglobins of the instant invention can be used to remove oxygen from solutions requiring the removal of oxygen (Donaventura and Bonavenhtra, U.S. Pat. No. 4,343,715, incorporated herein by reference) and as reference standards for analytical assays and instrumentation (Chiang, U.S. Pat. No. 5,320, 965, incorporated herein by reference) and other such in vitro applications known to those of skill in the art.

In a further embodiment, the multimeric hemoglobins of the present invention can be formulated for use in therapeutic applications. Such formulations suitable for the multimeric hemoglobins of the instant invention are described in Milne, et al., WO 95/14038 and Gerber et al., PCT/US95110232, both herein incorporated by reference. Pharmaceutical compositions of the invention can be useful for, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection.

For example, the multimeric hemoglobins of the present invention can be used in compositions useful as substitutes for red blood cells in any application that red blood cells are used. Such multimeric hemoglobins of the instant invention formulated as red blood cell substitutes can be used for the treatment of hemorrhages, traumas and surgeries where blood volume is lost and either fluid volume or oxygen carrying capacity or both must be replaced. Moreover, because the multimeric hemoglobins of the instant invention can be made pharmaceutically acceptable, the multimeric hemoglobins of the instant invention can be used not only as blood substitutes that deliver oxygen but also as simple volume expanders that provide oncotic pressure due to the presence of the large hemoglobin protein molecule. In a further embodiment, the multimeric hemoglobins of the instant invention can be used in situations where it is desirable to limit the extravasation of the hemoglobin-based blood substitute. Thus, the multimeric hemoglobins of the instant invention can act to transport oxygen as a red blood cell substitute, while reducing the adverse effects that can be associated with excessive extravasation. Moreover, the multimeric hemoglobins of the present invention can be synthesized with a specific and controlled high molecular weight (i.e., timers, tetramers, pentamers, etc.).

A typical dose of multimeric hemoglobins as blood substitutes can be from 10 mg to 5 grams or more of multimeric hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, and the particular purpose to be achieved according to the determination of the skilled artisan in the field.

Administration of multimeric hemoglobins can occur for a period of seconds to hours depending on the purpose of the hemoglobin usage. For example, as an oxygen delivery vehicle, the usual time course of administration is as rapid as possible. Typical infusion rates for hemoglobin solutions as blood replacements can be from about 100 ml to 3000 ml/hour.

In a further embodiment, the multimeric hemoglobins of the instant invention can be used to treat anemia, both by providing additional oxygen cawing capacity in a patient that is suffering from anemia, and by simulating hematopoiesis. When used to stimulate hematopoiesis, administration rates can be slow because the dosage of hemoglobin is much smaller than dosages that can be required to treat hemorrhage. Therefore the hemoglobin of the instant invention can be used for applications requiring administration to a patient of large volumes of hemoglobin as well a in situations where only a small volume of the multimeric hemoglobins of the instant invention is administered.

Because the distribution of the multimeric hemoglobins in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas. downstream of thrombi, sickle cell occlusions, arterial occlusions, angioplasty balloons, surgical instrumentation and the like. Because of this broad distribution in the body, the hemoglobins of the instant invention may also be used to deliver drugs and for in vivo imaging.

The multimeric hemoglobins of the instant invention can also be used as replacement for blood that is removed during surgical procedures where the patient's blood is removed and saved for reinfusion at the end of surgery or during recovery (acute normovolemic hemodilution or hemoaugmentation). In addition, the multimeric hemoglobins of the instant invention can be used to increase the amount of blood that may be predonated prior to surgery, by acting to replace some of the oxygen carrying capacity that is donated.

Under normal physiological conditions, nitric oxide is not produced in excess amount. However, certain disease states ae associated with excess nitric oxide production. Such conditions include septic shock and hypotension. In these cases, the multimeric hemoglobins of the present invention can be used to remove excess nitric oxide.

Additionally, the multimeric hemoglobins of the instant invention can be used in applications where oxygen delivery is not required. For example, the multimeric hemoglobins of the instant invention can be used for the delivery of drugs or imaging agents, as described in PCT publication number WO 93/08842, herein incorporated by reference. The multimeric hemoglobins of the instant invention can form oligomers of high molecular weight, and therefore can be used as oncotic agents, either alone or in combination with other oncotic agents. Moreover, because the globins of the instant invention bind heme, they can be used to provide heme to an in vivo or in vitro system in need thereof.

EXAMPLES

The following examples are provided by way of describing specific embodiments of the present invention without intending to limit the scope of the invention in any way.

Example 1

Construction of di di-alpha Gene Construct linked by a 7 amino acid linker (SGE 939)

A. Construction of pTZ19U/705 Mutants rHb0.1 genes were cloned as a BamHI/HindIII DNA fragment into pTZ19U (BioRad, Hercules, Calif.). This construct was then transformed using a modified process of the Hanahan protocol (Hanahan, *J. Mol. Biol.,* 166:557 (1983)) into CJ236 *E. coli* strain (BioRad). The Hanahan transformation buffer contained 45 mM $MnCl_2$, 60 mM $CaCl_2$, 40 mM KOAc, 620 mM sucrose, 15% glycerol and 100 mM rubidium chloride. A 5 ml culture of an *E. coli* strain was started in 2×TY broth from an isolated colony and cultured overnight. Then, 200 ml of 2×TY broth was inoculated with 2 ml of the overnight culture and incubated at 37° C. with vigorous shaking for 2.5 hours. The culture was then transferred to two 300 ml centrifuge tubes and placed on ice for 15 minutes. Cells were pelleted in a centrifuge at 8K rpm, 4° C., for 10 minutes and the supernatant was poured off. The cells were gently but thoroughly resuspended in 80 ml transformation buffer. The cells were again pelleted at 8K rpm, 10 minutes at 4° C. The cells were gently resuspended in 20 ml of ice-cold transformation buffer and left on ice for 30–60 minutes. Cells were aliquoted in buffer into twenty 1 ml tubes. The cells were quickly frozen on dry ice and stored at −80° C.

Single-stranded DNA containing uracil substitutions was isolated and oligonucleotide-directed mutagenesis was performed using the Muta-gene Kit (BioRad, Hercules, Calif.) and standard protocols according to the manufacturer's instructions. Two pTZ19U/705 clones were prepared as follows.

The first pTZ19U/705 clone was prepared using oligonucleotide JD29 (ACC GTT CTG ACT AGT AAA TAC CGT TAA TGA [SEQ. ID. NO. 3]). This oligonudeotide created a unique SpeI site in the end of the di-alpha domains. A second pTZ19U/705 clone was prepared using oligonudeotides JD28 (5'-GGA GGT TAA TTA ATG CTG TCT CCT GCA GAT-3' [SEQ. ID. NO. 4]) and JD30 (5'-CTG GTG GGT AAA GTT CTG GTT TGC GTT CTG-3' [SEQ. ID. NO. 5]). The resulting clone incorporated a unique PstI site in the di-alpha genes and removed an SpeI site in the beta domain.

B. Assembly of the di di-alpha gene construct

The assembly of di di-alpha gene construct was accomplished by removal of a di-alpha gene cassette from the first pTZ19U/705 clone using BamHI/SpeI enzymes and gel purification of the DNA fragment. A second pTZ19U/705 clone was cut with SpeI/BglII enzymes to give a second di-alpha gene cassette with the 5' end of the beta gene, which was also purified. These were then further ligated together with annealed oligonudeotides JA113 and JA114 to create a di di-alpha cassette with a 7 amino acid fusion peptide linker linking the two di-alpha globins.

JA113: 5'-CT AGT AAA TAC CGA TCG GGT GGC TCT GGC GGT TCT GTT CTG TCT CCT GCA-3' (SEQ. ID. NO.6).

JA114: 5'-GG AGA CAG AAC AGA ACC GCC AGA GCC ACC CGA TCG GTA TTT A-3' (SEQ. ID. NO.7).

This di di-alpha cassette was then ligated as a BamHI/Bgm fragment into pSGE705 (described in PCT publication number WO 95/14038, herein incorporated by reference) that had the rHb1.1 genes removed as a BamHI/BglII fragment. The resulting di di-alpha plasmid (pSGE1000) was transformed into SGE1661 (also described in PCT publication number WO 95/14038) using the modified Hanahan's protocol described above to create SGE939. Two other plasmids were also constructed using the same methods described above, pSGE1006 and pSGE1008. pSGE1006 corresponds to pSGE1000, except that the linker linking the two di-alpha regions was excised as an SpeI/PstI fragment and replaced with a synthesized region encoding a 14 amino acid linker of the following sequence:
GlyGlySerGlyGlySerGlyGlySerGlyGlySerlyGly (SEQ. ID. NO.8)

pSGE1008 was created in the same fashion as pSGE1006, except that the replacement linker was a 16 amino acid linker of the following sequence:
SerGlyGlySerGlyGlySerGlyGlySerGlyGlySerGlyGlySer (SEQ. ID. NO.9)

Example 2
Construction of a High Copy Plasmid (pSGE 720)

The construction of pSGE720 was performed in two stages. First, the pUC origin of replication was introduced to create plasmid pSGE715. Then, the lacI gene was deleted from the plasmid and replaced with a short oligonucleotide containing several convenient restriction sites to create plasmid pSGE720.

A. Construction of pSGE715

The pUC origin of replication was introduced to create plasmid pSGE715 through pSGE508, which is identical to pSGE509 (described in PCT publication WO95/14038) with the exception of a single base pair substitution at base 602 (G→A). The substitution changes the pBR322 origin of replication to a pUC19 origin of replication.

Plasmids pSGE508 and pSGE705 (pSGE705 is described in PCT publication WO95/14038) were digested to completion with restriction enzymes BamHI and HindIII, according to the manufacturer's instructions (New England Biolabs.). The plasmid, pSGE508, was digested first with BamHI to completion, then Hindi was added, and the digestion continued. The pSGE705 digest was purified with Promega Magic DNA Clean-up protocols and reagents (Promega, Madison, Wis.) and further digested to completion with BglI, according to the manufacturer's instructions (New England Biolabs). The enzymes in both pSGE508 and pSGE705 digests were inactivated by heating at 67° C. for 10 minutes, then the DNA was pooled and purified using Promega Magic DNA Clean-up protocols and reagents. The DNA was suspended in ligation buffer, T4 DNA ligase was added to one aliquot, and the DNA was incubated overnight at 16° C. SGE1661 cells were made competent by the method of Hanahan, using rubidium chloride (Hanahan, D., 1985. In *DNA Cloning; A Practical Approach* (Glover, D. M., ed.) vol. 1, pp.109–135, IRL Press, Oxford), and transformed with the ligation mix according to the Hanahan protocol. Transformants were selected by plating the cells on LB plates containing 15 g/ml tetracycline. Candidates were screened by restriction digestion to determine the presence of the rHb1.1 genes, and sequencing to detect the pUC origin of replication. Several candidates were identified, and the resulting plasmid was named pSGE715; pSGE715 in *E. coli* strain SGE1661 (ATCC accession number 5554S) was called SGE1493.

B. Construction of pSGE72M

The lad gene was deleted from pSGE715 and replaced with a short oligonucleotide containing several convenient restriction sites by the following steps. First, plasmid pSGE715 was digested to completion with restriction enzymes BamHI and NotI, according to the manufacturer's instructions (New England Biolabs). The pSGE715 digest was purified with Promega Magic DNA Clean-up protocols and reagents. The DNA was mixed with annealed, kinased oligonucleotides, CBG17+CBG18, and suspended in ligation buffer.

CBG17=(5'-3')
GGCCGCCTTAAGTACCCGGGTTTCTGC-
GAAAGCCCGCTTAATGCGGGCTTTTTTTCCTTAGG
(SEQ. ID. NO. 10)

CBG16=(5'-3')
GATCCCCTAAGGAAAAAAGCCCGCT-
CATTAGGCGGGCTTTCTGCAGAAAC-
CCGGGTACTTAAGG (SEQ. ID. NO. 1)

T4 DNA ligase was added to one aliquot, and the DNA was incubated overnight at 16° C. SGE1821 cells were made competent by the method of Hanahan using rubidium chloride and transformed with the ligation mix according to the Hanahan protocol. Any competent cells could have been used for screening. Transformants were selected by plating the cells on LB plates containing 15 g/ml tetracycline. Candidates were screened by restriction digestion using PstI and SmaI to detect the presence of the new linker and the absence of the lad gene, and sequenced to detect the pUC origin of replication and the absence of the lad gene. Several candidates were identified, and the resulting plasmid was named pSGE720. The plasmid pSGE720 in SGE1675 was denoted SGE1464. SGE1675 is congenic with SGE1661: that is, SGE1675 contains the ladI$^{q1}$ allele which was introduced by a series of P1 transductions.

Example 3
High copy Di di-alpha Construct (SGE 946)

A second plasmid containing the di di-alpha hemoglobin genes was created using pSGE720 as the vector. The di di-alpha gene cassette from pSGE1000 (described in Example 1) was removed as a BamHI/HindIII fragment and gel purified. The vector pSGE720 was also cut with BamHI/HindIII and the rHb1.1 genes removed. The vector was gel purified. The di di-alpha cassette was ligated into the pSGE720 vector, resulting in a new vector pSGE1004. The same procedure was utilized to make a high copy number version of the di-di-alpha construct linked with a 14 amino acid linker by removal of the BamHI/HindIII fragment from pSGE1006 and placement into the pSGE715 vector to create vector pSGE 1010. The procedure was repeated a third time using instead the BamHI/HindIII fragment from pSGE1008 to create a high copy version of di di-alpha globin linked with a 16 amino acid linker (pSGE1011).

Example 4

Dialpha-GCN4-dialpha fusion (SGE 954 and SGE 955)

Modified hemoglobins were produced by fermentation of the *E. coli* strain SGE 1661 (ATCC Accession Number 55545) carrying the plasmid pSGE 1012 or 1013. Strain SGE 1661 carrying the plasmid pSGE 1012 was denoted SGE 954 and SGE1661 carrying the plasmid pSGE 1013 was denoted SGE 955. Constructions of pSGE 1012 and 1013 are described below.

Materials.

Oligonucleotides were synthesized on an Applied Biosystems DNA Synthesizer Model 392 (Foster City, Calif.). The oligonudeotides used in preparing pSGE 1012 and pSGE 1013 are listed in Table 1. Restriction endonudeases were purchased from New England Biolabs (Beverly, Massachusetts) and used according to manufacturer's specifications. T4 DNA Ligase was purchased from either New England Biolabs or Gibco-BRL (Gaithersburg, Mass.) and used according to manufacturer's specifications.

Media used are described in J. H. Miller (*Experiments in Molecular Genetics*. Cold Spring Harbor Press, (1972) Cold Spring Harbor, N.Y.). and J. H. Miller (*A Short Course in Bacterial Genetics*. (1992) Cold Spring Harbor Press, Cold Spring Harbor, N.Y.). Acridine orange, ampicillin and kanamycin sulfate were purchased from Sigma Chemical Co. (St. Louis, Mo.). Tetracycline was purchased from Aldrich Chemicals (Mflwdukee, Wis.).

Genetic and Molecular Biological Procedures.

Standard bacterial genetic procedures were performed as described in J. H. Miller (*Experiments in Molecular Genetics.* (1972) Cold Spring Harbor Press, Cold Spring Harbor, N.Y.) and J. H. Miller (*A Short Course in Bacterial Genetics.* (1992) Cold Spring Harbor Press, Cold Spring Harbor, N.Y.). Standard molecular biology procedures were performed as described by Sambrook (Sambrook et al., *Molecular Cloning.* (1989) Cold Spring Harbor Press, Cold Spring Harbor, N.Y.).

Plasmid DNA Transformation.

Plasmids were transformed into SGE 1661 cells that had made competent by the calcium chloride method. The DNA ligations described below were placed on ice. The competent cells were added (0.2 mls) and allowed to incubate for 45 minutes, then the cell/DNA mixtures were heat shocked for 2 minutes at 42° C. After adding 1 ml of LB broth, the cells were incubated at 37° C. for 1 hour. The cells were spread on LB+tetracycline (15 micrograms/ml) plates and incubated overnight at 37° C. Isolated colonies were analyzed for the presence of recombinant plasmids.

TABLE 1

Oligonucleotides

| Oligo | Sequence (5'-3') | Description |
|---|---|---|
| SAC67 | CTAGTAAATACCGTGGTGGTTCTG | GCN4 LINKER |
| SEQ. ID. NO. 12 | GTGGTTCTGGTGGTTCTGGCGGCC | TOP STRAND |
| SAC68 | GCCTGAAACAGCTGGAAGACAAACT | GCN4 TOP STRAND |
| SEQ. ID. NO. 13 | GGAAGAACTGCTGTCTAAACTGTAC | |
| SAC69 | CACCTGGAAAACGAACTGGCTCGTCT | GCN4 TOP STRAND |
| SEQ. ID. NO. 14 | TAAGAAACTGTGCGGTGAACGTGGT | |
| SAC70 | GGTTCTGGTGGTTCTGGTGGTTCTGGT | GCN4 TOP STRAND |
| SEQ. ID. NO. 15 | GGTGTTCTGTCTCCTGCA | |
| SAC71 | GGAGACAGAACACCACCAGAACCACC | GCN4 BOTTOM STRAND |
| SEQ. ID. NO. 16 | AGAACCACCAGAACCACCA | |
| SAC72 | CGTTCACCGCACAGTTTCTTAAGACG | GCN4 BOTTOM STRAND |
| SEQ. ID. NO. 17 | AGCCAGTTCGTTTTCCAGGTGGTACA | |
| SAC73 | GTTTAGACAGCAGTTCTTCCAGTTTG | GCN4 BOTTOM STRAND |
| SEQ. ID. NO. 18 | TCTTCCAGCTGTTTCAGGCGGCC | |
| SAC74 | GCCAGAACCACCAGAACCACCAGAA | GCN4 BOTTOM STRAND |
| SEQ. ID. NO. 19 | CCACCACGGTATTTA | |
| SAC75 | CACCTGGAAAACGAACTGGCTCGTCT | GCN4 TOP STRAND |
| SEQ. ID. NO. 20 | TAAGAAACTGCTGGGTGAACGTGGT | NO CYSTEINE |
| SAC76 | CGTTCACCCAGCAGTTTCTTAAGACG | GCN4 BOTTOM STRAND NO CYSTEINE |
| SEQ. ID. NO. 21 | AGCCAGTTCGTTTTCCAGGTGGTACA | |

Construction of cloning cassette.

Complementary phosphorylated oligonucleotides (SAC67/SAC74; SAC68/SAC73; SAC69/SAC72; SAC70/SAC71) were annealed to create the cysteine containing cassette, and complementary phosphorylated oligonudeotides (SAC67/SAC74; SAC68/SAC73; SAC75/SAC76; SAC70/SAC71) were annealed to create the no cysteine cassette. The oligonucleotides were annealed by the following procedure: equimolar amounts of each phosphorylated oligonucleotide were mixed in 50 microliter 20 mM Tris-HCl pH 7.5/2 mM $MgCl_2$/50 mM NaCl and incubated at 95° C. for 5 minutes. The oligonudeotide solutions were cooled from 95° C. to 30° C. over 60 minutes, then transferred to an ice bath. Pairs of annealed oligomers (SAC67/SAC74+SAC68/SAC73; SAC69/SAC72+SAC70/SAC71; and SAC75/SAC76+SAC70/SAC71) were then ligated overnight at 16° C. with T4 DNA ligase to yield three cloning halves of the two cloning cassettes. Finally, the two cassettes were constructed by ligating (SAC67/SAC74+SAC68/SAC73) to either (SAC69/SAC71+SAC70/SAC71) or (SAC5/SAC76+SAC0/SAC71) with T4 DNA ligase at 16° C. overnight. The complete cassettes were amplified by polymerase chain reaction with oligonucleotides JD38 (5'-CGCACTAGTAAATACCGTGGT-3' [SEQ. ID. NO. 22]) and JD39 (5'-CGCCTGCAGGAGACAGAACAC-3' [SEQ. ID. NO. 23]). This amplification created enough DNA from each of the two full length cassettes for the separate cloning of each cassette as an SpeI/PstI fragment. The digested DNA cassettes were gel-purified with a 2% agarose gel and purified by a Wizard DNA cleanup kit (Promega, Madison, Wis.).

Construction of pSGE 1012 and 1013.

The final vectors were constructed in two steps to facilitate DNA sequencing of the GCN4 domains. The first vector, pBluescript (Stratagene, La Jolla Calif.) was cut with SpeI/PstI and the vector gel-purified using a 1% agarose gel. The vector DNA was electro-eluted and purified using a Wizard DNA cleanup kit (Promega). The two DNA casettes were ligated into pBluescript with T4 DNA ligase for 2 hours at 25° C. The ligations were transformed into DH5 alpha competent cells. Subclones were screened by restriction analysis for presence of the GCN4 cassettes. The GCN4/pBluescript plasmids were sequenced by di-deoxy DNA sequencing with a Sequenase v 2.0 kit (United States Biochemical, Inc., [USB] Cleveland, Ohio). Two correct clones were cut with SpeI/PstI restriction enzymes and the 194 base pair GCN4 cassettes gel-purified with a 1% agarose gel. The bands were excised from the gel, electro-eluted and purified with a Wizard DNA cleanup kit (Promega).

The vector pSGE 1011, described above in Example 3, was cut with SpeI/PstI restriction enzymes to remove the di-di alpha fusion domain. The residual vector was gel purified with a 1% agarose gel. The vector band was excised, electro-eluted and purified using a Wizard DNA cleanup kit (Promega). The two GCN4 cassettes were ligated into the pSGE1011 vector at 25° C. for 2 hours. SGE 1661 competent cells were transformed with the ligations of pSGE 1011 and GCN4 cassettes (cysteine and no cysteine). Sub-clones were screened for the presence of the GCN4 cassettes by restriction analysis. Positive clones were streak isolated on LB+tetracycline (15 micrograms/ml). Isolated colonies were used to make seed stocks, which were frozen at −80° C. The strains containing the plasmids were denoted SGE 954=SGE 1661+pSGE 1012 (with cysteine) and SGE 955=SGE 1661+pSGE 1013 (no cysteine). The final amino acid sequence of the GCN4 oligomerizing domains encoded by the ligated oligonucleotides described above are listed below. Note that the terminal amino acids are in parentheses because the oligonudeotides encode only part of the codon for those residues because the restriction enzyme cut sites are in the middle of those codons, thus only that part of the codon which makes up the proper sticky end for cloning is encoded by the cassette.

GCN4 with Cys:
(Thr)
SerLysTyrArgGlyGlySerGlyGly-
SerGlyGlySerGlyGlyArgLeuLysGlnLeu
GluAspLysLeuGluGluLeuLeu-
SerLysLeuTyrHisLeuGluAsnGluLeuAlaArgLeuLys
LysLeuCysGlyGluArgGlyGlySerG-
lyGlySerGlyGlySerGlyGlyValLeuSerProAla (Asp)
(SEQ.ID.NO.24)

GCN4 no Cys:
(Thr)
SerLysTyrArgGlyGlySerGlyGly-
SerGlyGlySerGlyGlyArgLeuLysGlnLeu
GluAspLysLeuGluGluLeuLeu-
SerLysLeuTyrHisLeuGluAsnGluLeuAlaArgLeuLys
LysLeuLeuGlyGluArgGlyGlySerG-
lyGlySerGlyGlySerGlyGlyValLeuSerProAla (Asp)
(SEQ.ID.NO.25)

B. Fermentations

Fermentor Inoculum(5000 mL broth in 2 L shake flasks)

To prepare the fermentor inoculum, seed stock was thawed. Seed stock (100 µl) was grown up in 500 ml of DM59 in an Erlenmeyer flask at 37° C. in a 1 inch rotary shake (275 to 300 rpm) for 8 to 10 hours. DM59 media is: 3.34 g/L $KH_2PO_4$, 5.99 g/L $K_2HPO_4$, 1.36 g/L $NaH_2PO_4.H_2O$ 1.95 g/L $Na_2HPO_4$, and 1.85 g/L $(NH_4)SO_4$ which are sterilized. After sterilization, a trace metal solution which is composed to yield the following final concentrations; 917 mg/L tripotassium citrate, 220 mg/L trisodium citrate, 185 mg/mi $FeCl_3.6H_2O$, 14.8 mg/ml $ZnCl_2$, 2.2 mg/ml $CoCl_2.6H_2O$, 1.8 mg/ml $Na_2MoO_4.2H_2O$, 18.6 mg/L $MnCl_2$, 44.7 mg/mL $CaCl_2.2H_2O$, 10.1 mg/ml Cu(II) $SO_4.5H_2O$, and 100.2 mg/L $H_3PO_4$ was added to a solutions, that when added to the flask yields a final concentration of 0.69 g/L tripotassium citrate, 0.264 g/L trisodium citrate and 0.379 g/L $MgSO_4$, $7H_2O$. Note all concentrations are final concentrations in the fermentor or flask. In addition, the following components were added after sterilization to achieve the final concentrations indicated: 9.4 mg/L tetracycline, 263 mg/L thiamine, and polypropylene glycol 2000.

Fermentor (100 L volume)

2000 mL of the Fermentor Inoculum was then aseptically transferred to a 100-liter Biolafitte fermentor containing 54 L of DM59 medium described above.

The fermentor was run at 30±1° C., controlling dissolved oxygen at 20% and glucose between 0–6 g/L. At OD 30±2, induction occurred by lowering the temperature of the fermentor to 26° C., adding 43.5 mL of 100 mM Isopropyl thiogalactoside (IPTG) and 73 mL of 50 mg/mL hemin. At 3 hours post induction, 96 mL of 50 mg/mL hemin was added, at 6 hours post induction, 125 mL of 50 mg/mL hemin was added, at 9 hours post induction, 125 mL of 50 mg/mL hemin was added and at 12 hours post induction, 125 mL of 50 mg/mL hemin was added. Harvest and further purification occurred at 16 hours post induction.

C. Purification

A Niro PANDA cell disruption device (Niro Hudson, Inc. Hudson, Wis.) was used for homogenization of the fermentation broth. Cells were lysed by a single passage through the homogenizer which was set at 800 bar. The lysate was sparged with CO gas, heated to 72° C. for 11 sec, then clarified using a rotary drum vacuum filter. The pH of the clarified lysate was adjusted to pH 8 with sodium hydroxide, and sufficient $Zn(OAc)_2$ was added to make the solution 24 mM in Zn(OAc)$_2$. The clarified lysate was then filtered in a CUNO (Meriden, Conn.) apparatus.

Chromatography.

All solutions were 4° C. and were adjusted to the correct pH at 4° C. 1000 mL of Chelating SEPHAROSE fast flow resin (Pharmacia, Piscataway, N.J.) was prepared by washing with 4 column volumes (CV) of distilled water. Flow through the column for all steps was 1000 mL/min. The resin was charged with 2 to 3 CV of 20 mM Zn(OAc)$_2$ followed by 2 to 3 CV of 200 mM NaCl. The lysate was loaded onto the column and washed with 1 CV of 20 mM Tris-HCl 50 mM NaCl pH 8.0; 2 CV of 20 mM Tris-HCl 500 mM NaCl pH 8.0; 2 CV of 20 mM Tris-HCl 50 mM NaCl pH 8.0; 10 CV of 10 mM imidazole 50 mM NaCl pH 7.2; 4 CV of 20 mM sodium phosphate 50 mM NaCl pH 6.5. The bound protein was then eluted with 20 mM Tris-HCl 15 mM EDTA pH 8.0. The purified protein solution was then concentrated to approximately 20 mg/mL and buffer exchanged with 68 CV of 20 mM Tris, pH 8.5 using a Filtron Technology Corp. (Northborough, Mass.) diafiltration apparatus equipped with 301D MWCO membranes to yield 1.1 gm of partially-purified fusion protein. Size exclusion chromatography (SEC) was performed on a Pharmacia (Piscataway, N.J.) XK50 column measuring one meter in length which was packed with Sephacryl S-200 HR. The mobile phase was phosphate buffered saline (pH 7.5) and the flow rate was regulated at 5 mL/min. The 180 µg of the partially purified fusion protein from the IMAC step described above was loaded onto the SEC column in a volume of 22 mL. Fractions containing larger sized rHb were pooled and concentrated in Amicon (Beverly, Mass.) Centriprep30 concentrators to yield 84 µg of fusion protein.

Protein analysis and characterization.

SEC-purified fusion protein was collected and globin chains were separated by C4 reverse phase high performance liquid chromatography on a Hewlett Packard model 1090 HPLC equipped with a Vydac 5µ 0.46×25 cm C4 column using a gradient of acetonitrile (ACN) in water (0.1% trifluoroacetic acid) as the mobile phase. The 75 min gradient elution was established as follows: 3 min at 30% ACN, a linear gradient from 30–37% ACN over 12 min, a linear gradient from 37–50% ACN over 60 min. The C4 chromatogram showed five prominent peaks eluting at 22 min, 38 min, 55 min, 58 min and 60 min respectively. The separated globins were analyzed by electrospray mass spectroscopy (Vestec, Inc., Houston, Tex.). The peak eluting at 22 min was identified as heme. The peak eluting at 38 min was identified as beta globin (observed mass=15912, calculated mass=15913). The peak eluting at 58 min was the expected dialpha-GCN4-dialpha fusion peptide (observed mass=66051, calculated mass=66026). The peaks eluting at 55 and 60 min did not give interpretable mass spectra. The peaks eluting between 55 and 60 min were all analyzed by 10 cycles of N-terminal amino add sequencing on a Porton Automated Edman sequencer (Porton Ingtruments, Tarzana, Calif.). All three peaks gave the expected N-terminal sequence for alpha globin. High performance size exclusion chromatography analysis performed on a Pharmacia SUPEROSE 12 column shows the fusion protein rung larger than a single rHb molecule. The retention times on this column for the fusion protein and rHb1.1 are 20.4 min and 25.2 min respectively.

Example 5

C-terminal di-alpha-GCN4 fusion (SGE947)

Gene synthesis.

A synthetic DNA cassette was synthesized which encodes the following amino add sequence:
SKYRPKPSTPPGSSRLKQLEDKLEELL-SKLYHLENELARLKKLCGER (SEQ. ID. NO. 26)
SKYR encodes the last four residues of the dialpha globin, PKPSTPPGSS encodes a linker sequence, and RLKQLED . . . KKLCGER encodes a mutant coiled-coil domain from the yeast transcription factor GCN4. In this GCN4 coiled-coil variant, all residues defining the hydrophobic interface between the helices in the coiled-coil are Leu (with the exception of a single Cys which is incorporated to provide a means to make a covalent link between two adjacent helices). The DNA cloning cassette was made to have SpeI and BspEI ends for insertion into pSGE1000 or derivatives. The cassette was contructed from the following synthetic oligomers:
SAC51 CTAGTAAATACCGTCCGAAACCATCTAC-CCCGCCGGGCTCTTCTC (SEQ. ID. NO.27)
SAC52 GTCTGAAACAGCTGGAAGATAAACTG-GAAGAACTGCTGAGCAAACTGTACCAC (SEQ. ID. NO.28)
SAC53 CTGGAAAACGAACTGGCTCGTCT-GAAAAAACTGTGCGGTGAAC (SEQ.ID.NO.29)
SAC54 GTTAATGATCTAGATAAGGAGG-TAAATATATGCACCTGACT (SEQ.ID.NO.30)
SAC55 CCGGAGTCAGGTGCATATATTTACCTCCTTAT (SEQ. ID. NO.31)
SAC56 CTAGATCATTAACGTTCACCGCA-CAGTTTTTTCAGACGAGC (SEQ.ID.NO.32)
SAC57 CAGTTCGTTTTCCAGGTGGTA-CAGTTTGCTCAGCAGTTCTTCCAGTTTATCTTCCAG (SEQ.ID.NO.33)
SACS8 CTGTTTCAGACGAGAAGAGCCCG-GCGGGGTAGATGGTTTCGGACGGTATTTA (SEQ.ID.NO.34)
Oligomers were annealed in pairs (SAC51:SAC58, SAC52:SAC57, SAC53-SAC56, SAC54:SAC55) to make dsDNA oligomers which were then sequentially annealed and ligated to form the cassette. The amino acid sequence of the domain coded for by the cassette is as follows:
(Thr)
SerLysTyrArgProLysProSerThr-ProProGlySerSerArgLeuLysGlnLeu
GluIspLysLeuGluGluILeuLeu-SerLysLeuTyruisLeuGluAsnG-luLeuxlaargLeuLysLysLeuCysGlyGluArg (SEQ. ID. NO.35)
Note that parenthesized N-terminal residue is not encoded by the oligonucleotide due to restriction sites, as discussed in Example 4. The next residues of SEQ. ID. NO. 35, SerLysTyrArg, are the four C-terminal residues of the fused di-alpha globin, which are then followed by the mutant GCN4 domain.

Following the GCN4 domain, the DNA of the cassette codes for two stop codons and a region of untranslated "spacer DNA." The spacer DNA would, if translated, code for the residues SerArg followed by another stop codon, and thereafter followed by the residues: GlyGlyGlyLysTyr (SEQ. ID. NO. 64). This spacer DNA, following the two stop codons at the C-terminus of the GCN4 domain, induces an XbaI site followed by a ribosome binding site used to initiate translation of beta globin. Following the untranslated "spacer DNA" is a region coding for the following N-terminus of the beta globin. MetHisLeuThr(ProGlu) (SEQ. ID. NO. 65)

Again, the parenthesized amino acids are part of the restriction site at the end of the cassette and therefore the coding region for these amino acids is not completed until the cassette is ligated in place.

The cassette was ligated as an SpeI/BspEI fragment into pSGE1000, which had been cut with SpeI and BspEI, (as described in Example 4). Transformants were identified and plasmid DNA (pSGE1005) containing the fusion of the modified GCN4 coiled-coil sequence to the 3' end of the dialpha globin gene was isolated. The sequence of the fusion was confirmed by dideoxy sequencing (Sequenase from USB). The pSGE1005 was transformed into the E. coli expression strain SGE1661 to make strain SGE947.

Gene expression.

SGE947 was grown at 30° C. in a 100 L fermentor using minimal medium as described in Example 4. At $OD_{600}$ of 30, 55 µM IPTG was added to the fermentation broth to induce expression of the fusion protein. Induction lasted 10 hr at a temperature of 28° C. Hemin stock at a concentration of 50 mg/mL was added at 0, 3 and 6 hr post induction in 73 mL, 96 mL and 125 mL aliquots.

Protein purification.

Following the induction period the cells were lysed using a Niro homogenizer. The lysate was sparged with CO gas, heated to 72° C. for 11 sec, then clarified using a rotary drum vacuum filter. The clarified lysate was filtered in a CUNO apparatus (Meriden, Conn.) and loaded onto a immobilized metal affinity column (IMAC) charged with Zn. Material which bound the resin was washed with the following buffers in this order: 20 mM Tris-HCl 50 mM NaCL pH 8.0; 20 mM Tris-HCl 500 mM NaCl pH 8.0; 20 mM Tris-HCl 50 mM NaCl pH 8.0; 10 mM imidazole 50 mM NaCl pH 7.2,e 20 mM sodium phosphate 50 mM NaCl pH 6.5. The bound protein was then eluted with 20 mM Tris-HCl 15 mM EDTA pH 8.0. The eluate was concentrated using a Filtron (Filtron Technology Corp., Northborough, Mass.) diafiltration apparatus to 25–50 mg/mL. The hemoglobins were separated by size exclusion chromatography (SEC) on Pharmacia (Piscataway, N.J.) S-200 and S-300 columns linked in parallel. Appropriate fractions were pooled and buffer exchanged into 20 mM Tris-HCl pH 8.8 by diafiltration. The SEC-purified protein was further purified by anion exchange chromatography on Q-SEPHAROSE (Pharmacia) resin. CO-recombinant hemoglobin (CO-rHb) was converted to oxy-rHb by several cycles of concentration/dilution using highly oxygenated phosphate buffered saline buffer and CENTRIPREP (Amicon, Beverly, Mass.) concentrators to a final concentration of 17–25 mg/mL.

Protein analysis and characterization.

SEC-purified fusion protein was collected and globin chains were separated by C4 reverse phase high performance liquid chromatography (RP-HPLC) on a Hewlett Packard model 1090 HPLC equipped with a Vydac 5µ 0.46×25 cm C4 column. The protein was separated using a gradient of acetonitrile (ACN) in water containing 0.1% trifluoroacetic acid (TFA) as the mobile phase. The 75 mil gradient elution was established as follows: 3 min at 30% ACN, a linear gradient from 30–37% ACN over 12 min, a linear gradient from 37–50% ACN over 60 min. The C4 chromatogram showed four prominent peak eluting at 24 min, 45 min, 55 min and 62 min respectively. The separated globins were analyzed by electrospray mass spectroscopy (ESMS) using a Vestec model ESMS (Houston, Texas) and automated N-terminal Edman sequencing (PI 2090E amino acid sequencer, Porton Instruments, Tarzana, Calif.).

ESMS analysis showed that the peak eluting at 24 min was heme. The peak eluting at 45 min was identified as beta-globin (observed mass=15914, calculated mass= 15913). The peak eluting at 55 min was a disulfide-bonded species where an intact fusion peptide was bound to a fragment of the fusion protein which included the GCN4 and linker regions and 4–5 amino acids of the dialpha globin (observed mass=40837, calculated mass for the fragments identified by amino acid sequencing–40733 and 40834) The peak eluting at 62 min was a mixture of fusion peptides bound to glutathione (observed mass 35571, calculated mass=35558) and the expected disulfide bonded fusion protein dimer (observed mass=70525, calculated mass= 70503). The oxygen affinity and cooperativity of Q-SEPHAROSE purified protein were determined at 37° C. using a Hemox analyzer (TCS Medical Products, Southampton, Pa.) using the methods described in granted U.S. Pat. No. 5,028,588. The observed P50 was 9.0 torr with an $n_{max}$ of 1.5. High performance SEC analysis performed on a Pharmacia SUPEROSE-12 column showed that the fusion protein eluted as a larger protein than a single recombinant hemoglobin molecule. The retention times on this column for the fusion protein and rHb1.1 were 21.6 min and 25.2 min respectively.

Example 6

Di-alpha-tetraZIP GCN4 fusion

A synthetic gene for the tetraZIP GCN4 oligomerization domain was designed based on the tetraZIP GCN4 leucine zipper sequence which is as follows:

RLKQIEDKLEEILSKLYHIENELARIKKLLGER (SEQ. ID. NO. 66)

The tetraZIP GCN4 domain was fused to the N- or C-terminus of di-alpha globin via the following peptide linker: GGSGGSGGSGG (SEQ. ID. NO. 67). In this GCN4 colied-coil variant residues in the hydrophobic a position of the heptad repeat are leucine, and all d position residues are isoleucine. the cloning cassette was made to have Spe I and Xba I ends for insertion into deriviatives of pSGE.

The synthetic gene for the C-terminal fusion gene was assembled from synthetic oligomers and cloned independently at the C-terminus and the N-terminus of dialpha globin. Cloning strategy was similar to Example 4. Molecular biology techniques and procedures were as described in Example 9 unless otherwise noted C-terminal tetraZIP GCN4 oligonucleotides:

EV171

5' GGGAAAGATAGGATCCACTAGTGGTG-GCTCTGGCGGCTCCGGTGGCTCCGTGGGCCG 3' (SEQ. ID. NO. 68)

EV172

5' TTTGATTTTAAGCTTCTAGACGTTCAC-CCAGCAGTTTTTTGATACGAGCCAGTTCGTTTTC 3' (SEQ. ID. NO. 69)

EV 173

5' GGTGGCTCCGTGGGCCGTCTGAAACA-GATCGAAGACAGCTGGAAGAAATCC 3' (SEQ. ID. NO. 70)

EV174

5' TTCGATCTGTTTCAGACGGCCOACGGAGCCACC 3' (SEQ. ID. NO. 71)

EV176

5' TGTCTAAACTGTACCACATCGAAMC-GAACTGGCTCGTATC 3' (SEQ. ID. NO. 72)

EV176

5' GATACGAGCCAGTTCGTrTCCGATGTGG-TACAGTTTAGACAGGATTTCTTOCAGTTTGTC 3' (SEQ. ID. NO. 73).

Complementary oligonucleotides were gel purified, phosphorylated, and annealed, forming fragments EV173/

174 and EV175/176. These two fragments were ligated to form a fragment that was then PCR amplified using primers EV171 and EV172 (0.2 μM each) using the AmpliTaq PCR (Perkin-Elmer) kit according to manufacturer's instructions. PCR cycle conditions: 95° C. 15 sec, 60° C. 15 sec, 72° C. 30 sec, 25 cycles. Amplified product was gel purified and cloned into pDC SK+ for sequence analysis. Sequence analysis was by ABI automated sequencer according to manufacturer's specification. The correct clone was digested with SpeI and Xba I, and the fragment containing the tetraZIP GCN4 gene was gel purified. The fragment was cloned into SpeI-XbaI digested pSGE1103, replacing We COMP domain with the tetraZIP GCN4 domain. The C-terminal tetraZIP GCN4-dialpha fusion with Presbyterian beta globin was designated pSGE1357. The BamHI-BspEI fragment from pSGE1357 containing dialpha-tetraZIP GCN4 was cloned into BamHI-BspEI digested pSGE768 as described in Example 4 to generate a plasmid co-expressing C-terminal tetraZIP-dialpha with Providence (K82D) beta, designated pSGE1358. This plasmid transformed into SGE1675 generated strain SGE2960.

N-terminal tetraZIP GCN4

The N-terminal tetraZIP domain DNA cassette was assembled from the -following oligonucleotides:

EV177
5' GTTATTCTATGGATCCTTMTTMCGTCT-GAAACAGATCGAAGACAAACTGGMGAMTCC 3' (SEQ. ID. NO. 74)

EV178
5' TTTATTTATTAMGCTTCTGCAGGCCAC-CGGAGCCACCGGAGCcGCCAGAGCCACCACGTTC 3' (SEQ. ID. NO. 75)

EV179
5' CGMGACAACTGGMGMATCCT-GTCTAAACTGTACCACATCGAAMCGMCTG 3' (SEQ. ID. NO. 76)

EV180
5' GTGGTACAGTTTAGACAGGATTICTTC-CAGTTTGTCTTTCG 3' (SEQ. ID. NO. 77)

EV181
5' GTCCGTATCAAAAAACTGCTGGG-TAACGTGGTGGCTCTGGCG 3' (SEQ. ID. NO. 78)

EV182
5' CGCCAGAGCCACCACGTTCACCCAG-CAGTTTTTTGATACGAGCCAGTTCGTTTTCGAT 3' (SEQ. ID. NO. 79)

Complementary oligonucleotides were gel purified, phosphorylated, and annealed to form fragments EV179/180 and EV181/182. The two fragments were ligated, and the resulting fragment was gel purified and amplified with PCR primers EV177 and EV178 (0.2 μM each) using the Ampli-Taq PCR kit (Perkin-Elmer) according to manufacturer's instructions. The amplified product was gel purified and cloned into pBC SK+ as a BamHI-HindIII fragment for sequence analysis. The clone with the correct DNA sequence was digested with PacI and Pst I, and the fragment containing the tetraZIP domain gene was gel purified. Prasmid pSGE1176, a derivabvc of p5GE1351 (Exmple9) with the PstI site upstream of the BamHI site removed, was digested with PacI and PstI, and the large fragment was gel purified. The tetraZIP fragment and the pSGE1176 fragment were ligated to generate plasmid pSGE1360 and transformed into SGE1675 to generate strain SGE2962. This plasmid encodes the N-terminal dialpha-tetraZIP GCN4 fusion with the Providence (K82D) beta globin.

Example 7

Di-alpha WTGCN4 fusion.

The wild-type leucine zipper sequence from GCN4 was cloned for comparison with the dialphaGCN4 fusion described in Example 5. The WT leucine zipper amino acid sequence is:

MKQLEDKVEELLSKNYHLENEVARLKKLVGER (SEQ. ID. NO. 80)

The domain was fused to the C-terminus of dialpha globin via the peptide linker:

GGSGGSGGSGG (SEQ. ID. NO. 81)

The domain-linker coding sequence was cloned as a synthetic DNA fragment. Cloning strategy and molecular biology techniques were as described in Example 9 unless otherwise noted.

The synthetic cloning cassette was assembled from the following oligonucleotides:

JE37 5' ACTAGTAAATACCGTGGTGGTTCTGGTG-GTTCTGGTGGTT3' (SEQ. ID. NO.82)

JE38 5' CTGTTTCATTCGACCACCAGAACCACCA-GAACCACCAGAA 3' (SEQ. ID. NO.83)

JE39 5' CTGGTGGTCGAATGAAACAGCTGGAAGA-CAAAGTTGAAGA 3' (SEQ. ID. NO.84)

JE40 5 GGTAGTFTAGACAGCAGTTCT-TCAACTTTGTCTTCCAG 3' (SEQ. ID. NO.85)

JE41 5' ACTGCTGTCTAAAAACTACCACCTG-GAAAACGAAGTTGCT 3' (SEQ. ID. NO. 86)

JE42 5' CCAACCAGTTTTTTCAGCGAGCAACT-TCGTTTTCCAGT 3' (SEQ. ID. NO.87)

JE49 5' CGTCTGAAAAAACTGGUGGTGAACGUAATGATCTA (3AT 3' (SEQ. ID. NO. 88)

JE44 5' GTGCATATATTTACCTCCTTATCTAGAT-CATTAACGTTCA 3' (SEQ. ID. NO.89)

JE66 5' CGCGCGGATCCAGTAATAACGTGGTGGT-TCTGGTGGTTCTGGTGG 3' (SEQ. ID. NO. 90)

JE68 5' CGCGTATATACGMGCTTTCTAGATTAU-TAACGTTCACCAACCAGTTTTTTCAG 3' (SEQ. ID. NO. 91)

Complementary oligonucleotides were gel purified, phosphorylated, and annealed to form fragments JE37/38, JE39/40, JE41/42, and JE42/43. Fragments 37/38 and 39/40 were ligated together, and fragments 41/42 and 43/44 were ligated together. The ligated fragments were gel purified, and the two fragments ligated to form one fragment. This fragments was purified by spin column (Qiagen) and amplified with primers JE66 and JE68 (1 μM each) using the AmpliTaq PCR kit (Perkin-Elmer) according to manufacturer's instructions. PCR cycle conditions were: 95° C. 15 sec, 60° C. 15 sec, 72° C. 15 sec, 25 cycles. Amplified product was spin-column purified and digested with Spe I and Xba I. The fr agment containing the linker-GCN4 coding sequence was gel purified and ligated with Spe I-Xba I digested pSGE1307 as described in Example 4. Transformants were screened by sequence analysis (ABI automated sequencer) and the correct plasmid designatad pSGE1318. This plasmid co-expresses the gene for Presbyterian beta globin.

The BamHI-BspEI fragment from pSGE1318 containing the dialpha globin-GCN4 fusion gene was subcloned into BamHI-BspEI digested pSGE768 as described in Example 4 to generate pSGE1320, which co-expresses the dialpha WTGCN4 fusion protein with Providence (K82D) beta globin. Transformation of this plasmid into SGE1675 generated strain SGE2820.

Example 8
Dialpha-p53 fusion (SGE 2802)
A. Construction of a Bacterial System for the Recombinant Production of rHb1.1 fused to the tetramerizing domain of p53

Modified hemoglobins were produced by fermentation of E. coli strain 1675, described above, carrying the plasmid pSGE 1304. Construction of pSGE 1304 is described below. Strain SGE 1675 carrying the plasmid pSGE 1304 was denoted SGE2802. Constructs were created using the techniques described in Example 4 unless otherwise noted.

TABLE 2

Oligonucleotides

| OLIGO | SEQUENCE (5'-3') | DESCRIPTION |
|---|---|---|
| SEQ. ID. NO. 36 | CTAGTAAATACCGTGGTGGTTCTGGTGGTT-CTGGTGGTTCTGGTGGTAACACCTCTT | P53 LINKER TOP STRAND |
| SAC60 SEQ. ID. NO. 37 | CTTCTCCGCAGCCGAAAAAAAAACCGCTGG-ACGGTGAGTACTTCACCCTGCAAATCC | P53 TOP STRAND |
| SAC61 SEQ. ID. NO. 38 | GTGGTCGTGAACGTTTCGAGATGTTTCGCG-AACTGAACGAAGCTCTGGAACTTAAGG | P53 TOP STRAND |
| SAC62 SEQ. ID. NO. 39 | ACGCTCAGGCTTAATGATCTAGATAAGGAG-GTAAATATATGCACCTGACT | P53 TOP STRAND |
| SAC63 SEQ. ID. NO. 40 | CCGGAGTCAGGTGCATATATTTACCTCCTT-ATCTAGATCATTAAGCCTGA | P53 BOTTOM STRAND |
| SAC64 SEQ. ID. NO. 41 | GCGTCCTTAAGTTCCAGAGCTTCGTTCAGT-TCGCGAAACATCTCGAAACGTTCACGA | P53 BOTTOM STRAND |
| SAC65 SEQ. ID. NO.42 | CCACGGATTTGCAGGGTGAAGTACTCACCGT-CCAGCGTTTTTTTTTCGGCTGCGGA | P53 BOTTOM STRAND |
| SAC66 SEQ. ID. NO. 43 | GAAGAAGAGGTGTTACCACCAGAACCACCAG-AACCACCAGAACCACCACGGTATTTA | P53 LINKER BOTTOM STRAND |

Construction of cloning cassette. Complementary phosphorylated oligonucleotides (SAC9/SAC66 ; SAC60/SAC65;, SAC61SAC64: SAC62/SAC63) were annealed according to the following procedure: equimolar amounts of each phosphorylated oligonucleotide were mixed in 20 μl of 20 mM Tris-HCl pH 7.5/2 mM MgCl$_2$/50 mM NaCl and incubated at 95° C. for 5 minutes. The oligonudeotide solutions were cooled from 95° C. to 30° C. over 60 min, then transferred to an ice bath. Pairs of annealed oligomers (SAC59/SAC66+SAC60+SAC65; SAC61/SAC64+SAC62/SAC63) were then ligated at 16° C. overnight with T4 DNA ligase to yield two halves of the cloning cassette. Finally, the cassette was constructed by ligating the two halves with T4 DNA ligase at 16° C. overnight. The amino acid sequence of the cassette is as follows:
(Thr) SerLysTyrArgGlyGlySerGlyGlyserGlyGlyserGlyGly AsnThrserserSerProGlnProLysLysLysProLeuAspGlyGlu TyrPheThrLeuGlnIleArgGlyArgGluArgPheGluMetPheAr gGluLeuAsnGluAlaLeuGluLeuLysAspAlaGlnAlandEndg erArgEndGlyGlyLysTyrMetfisLeuThr(ProGlu) (SEQ. ID. NO. 44)
Construction of pSGE 1304.
The p53 tetramerization domain coding sequence was designed with an Spe I site at the 5' end and a BspE I site at the 3' end. The Spe I site is in the dialpha gene; the synthetic gene encodes the last four amino acids of alpha globin, the p$^5$3 tetramerization domain, two translation termination codons, and the first five amino acids of beta globin.

The ligated cassette was purified by electrophoresis on 2.5% agarose. A 221 bp fragment corresponding to the expected length of the cloning cassette was excised and isolated by electroelution onto a diethylaminoethyl (DEAE) membrane (S&SNA45, Schleicher and Schuell, Inc. Keene, N H). The fragment was eluted from the membrane in 1 M Naa, 0.1 mM EDTA, 20 mM Tris-HCl pH 8.0 at 65° C and recovered by ethanol precipitation. The fragment was then phosphorylated using T4 polynucleotide kinase (NEB) and purified by Wizard DNA cleanup kit (Promega).

The cloning vector was prepared by digesting approximately 10 μg pSGE1004 with BspEI and Spe I (NEB). The ~3600 bp fragment was gel-purified on DEAE membrane as described above and precipitated with ethanol.

Approximately 100 ng of vector fragment were ligated with approximately 100 ng pS3 fragment (Ng T4 DNA ligase and buffer). One-tenth of the ligation mix was transformed into commercially prepared electrocompetent E. coli JS4 (Bio-Rad Laboratories, Hercules, Calif.) cells by electroporation using the BTX E. coli Transporator, per manufacturer's instructions (BTX, Inc., San Diego, Calif.). Transformants were screened for the presence of the p5$^3$ synthetic gene by restriction analysis. Verification of the correct p53 tetramerization domain gene sequence was by Sequenase v.2 kit according to the manufacturer's instructions (USB). The plasmid containing the correct p53 sequence was designated pSGE1304, and transformed into the production strain SGE1675. The resulting transformant was designated SGE2802.

Production of a protein approximately 39,000 daltons in size upon induction of SGE2802 with IPTG in a shake-flask culture grown according to Example 4 was determined by SDS-polyacrylamide gel electrophoresis. The culture was frozen and stored for 100 L fermentation as described in Example 4.

Protein was purified and separated by chromatography ad described in Example 4.

Protein analysis And characterization.

SEC-purified fusion protein wag collected and globin chains were separated by C4 reverse phase HPLC using a gradient of acetonitrile (ACN) in water (0.1% TFA) as the mobile phase as described above. The 75 min gradient elution is established as follows: 3 min at 30% ACN, a linear gradient from 3037% ACN over 12 min, a linear gradient from 37–50% ACN over 60 min. The C4 chromatogram showed three prominent peaks eluting at 22 min, 36 min and 46 min respectively. The separated globins were analyzed by electrospray mass spectroscopy. The peak eluting at 22 min is heme. The peak eluting at 36 min is beta-globin (observed mass=15911, calculated mass=15913). The peak eluting at 46 min is the expected dialpha-p53 fusion peptide (observed mass=36291, calculated mass=36280). HPSEC analysis performed on a Pharmacia SUPEROSE 12 column demonstrated the fusion protein runs larger than a single rHb molecule. The retention times on this column for the fusion protein and rHb1.1 are 21.0 min and 25.2 min respectively. Particle size of SEC-purified fusion protein was determined by laser light scattering using a NICOMP 370 HPL Submicron Particle Sizer (Santa Barbara, Calif.). Mean diameter for the fusion protein was 10.9 nm (compared to rHb1.1 which is typically 5.5 to 6 nm).

Example 9

Di-alpha-COMP fusion

A synthetic gene for the COMP oligomerization domain was designed from the published amino acid sequence of the murine domain (Efimov et. al., *FEBS Letters* 341 (19%) 54 58);

QGQIPLGGDLAPQMLRELQETNAALQD-VRELLRQQVKEITFLKNTVMECDACGMQ-PARTPGLSV (SEQ. ID. NO. 45)

A similar gene may be designed from the nearly identical amino acid sequence of the human COMP domain (Newton, et. al., *Genomics* 24, 435–439 (1994), Genbank accession # 132137):

QGQSPLGSDLGPQMLRELQETNAALQD-VRDWLRQQVREITFLKNTVMECDACGM-QQSVRTGLPSV (SEQ. ID. NO. 46)

The codons encoding the peptide sequence were optimized for expression in *E. coli* according to published codon usage tables (Sharp et. al., *Nucleic Acids Research* 16 no. 17, p. 8207 (1988)), except codons used to engineer restriction enzyme recognition sequences. The oligonucleotides used in preparing COMP domain-dialpha fusion genes are listed in Table 3. All procedures were as described in Example 4 unless otherwise noted.

TABLE 3

| | Oligonucleotide Sequence (5'-3') |
|---|---|
| JE21 SEQ. ID. NO. 47 | TAATGCAGGGTCAGATCCCACTGG |
| JE22 SEQ. ID. NO. 48 | GTGGGATCTGACCCTGCATTAAT |
| JE23 SEQ. ID. NO. 49 | GTGGTGACCTGGCTCCGCAGATGCTGCGTGAACTCCAGGAAACCAACGCT GCTCTC |
| JE24 SEQ. ID. NO. 50 | GTTGGTTTCCTGGAGTTCACGCAGCATCTGCGGAGCCAGGTCACCACCCA |
| JE25 SEQ. ID. NO. 51 | CAGGACGTACGTGAACTGCTGCGTCAGCAGGTTAAAGAAATCACCTTCCT GAAAAACAC |
| JE26 SEQ. ID. NO. 52 | GAAGGTGATTTCTTTAACCTGCTGACGCAGCAGTTCACGTACGTCCTGGA GAGCAGC |
| JE27 SEQ. ID. NO. 53 | CGTTATGGAATGCGATGCATGCGGTATGCAGCCGGCTCGTACCCCGGGGC |
| JE28 SEQ. ID. NO. 54 | TCAGCCCCGGGGTACGAGCCGGCTGCATACCGCATGCATCGCATTCCATA ACGGTGTTTTTCAG |
| JE29 SEQ. ID. NO. 55 | CGTTATGGAAGCTGATGCAGCTGGTATGCAGCCGGCTCGTACCCCGGGGC |
| JE30 SEQ. ID. NO. 56 | TCAGCCCCGGGGTACGAGCCGGCTGCATACCAGCTGCATCAGCTTCCATA ACGGTGTTTTTCAG |
| JE31 SEQ. ID. NO. 57 | TGAGCGTTGGTGGTTCTGGTGGTTCTGGTGGTTCTGGTGGTGTTCTGTCT CCTGCA |
| JE32 SEQ. ID. NO. 58 | GGAGACAGAACACCACCAGAACCACCAGAACCACCAGAACCACCAACGC |
| JE33 SEQ. ID. NO. 59 | TGAGCGTTTAATAATCTAGATAAGGAGGTAAATATATGCACCTGACT |
| JE34 SEQ. ID. NO. 60 | CCGGAGTCAGGTGCATATATTTACCTCCTTATCTAGATTATTAAACGC |

TABLE 3-continued

| | Oligonucleotide Sequence (5'-3') |
|---|---|
| JE48<br>SEQ. ID. NO. 61 | CTAGTAAATACCGTGGTGGTTCTGGTGGTTCTGGTGGTTCTGGTGGTCAG<br>GGTCAGATCCCACTGG |
| JE49<br>SEQ. ID. NO. 62 | GTGGGATCTGACCCTGACCACCAGAACCACCAGAACCACCAGAACCACCA<br>CGGTATTTA |
| JE50<br>SEQ. ID. NO. 112 | GGAGGTTAATTAATGCAGGGTCAGATCCC |
| JE51<br>SEQ. ID. NO. 113 | CGTTGGTTTTATCTGCAGGAGACAGAACACC |
| JE55<br>SEQ. ID. NO. 114 | GCGGATCCACTAGTAAATACCGTGGTGGTTCTGGTGG |
| JE65<br>SEQ. ID. NO. 115 | GCGCGCGTATATACGAAGCTTTCTAGATTATTAAACGCTCAGCCCCGG |
| JE66<br>SEQ. ID. NO. 116 | CGCGCGGATCCACTAGTAAATACCGTGGTGGTTCTGGTGGTTCTGGTGG |

Four constructions for expression of a dialpha globin-COMP oligomerization domain fusion protein were designed. The constructions were based on the high-copy pSGE715 expression vector described in Example 3.
The four constructions were:
Two variants of the COMP domain fused to the amino terminus of dialpha:
(1) the published COMP domain amino acid sequence (Efimov, et. al., *FEBS Letters* 341 (1994) 54–58), which includes two cysteines, and
(2) the COMP domain with alanine residues replacing the cysteines.
Two variants of the COMP domain fused to the carboxy terminus of dialpha:
(3) the COMP domain with cysteines, and
(4) tie COMP domain with alanines replacing cysteines.
All constructs included engineered restriction sites to allow modification of linker sequence between the COMP domain and dialpha globin. The linker used initially was (Gly-Gly-Ser)3-Gly-Gly (SEQ. ID. NO. 63).
Amino terminal fusions:
Gel purified complementary oligonudeotides were annealed in 10 mM Tris-HCl pH 8.0, 1 mM EDTA. Equimolar amounts of oligonudeotides were mixed, heated to 65° C. for 15 minutes, transferred to 37° C. for 15 minutes, then held on ice one hour. The double-stranded DNA fragments formed by the annealed complementary oligomers are listed in Table 4:

The annealed oligonucleotides were phosphorylated using NEB polynucleotide kinase according to manufacturer's specification.
Assembly of COMP pentamerization domain synthetic gene:
The fragments were ligated (T4 DNA ligase, NEB) in the following steps:
1. JE23/24+JE25/26+JE27/28 (contains cysteines) JE23/24+ JE25/26+JE29/30 (Cyan→Ala)
2. The resulting 175 bp DNA fragments were gel purified onto DEAE membrane as described in Example 8.
3. Each fragment was ligated with fragments 21/22 and 31/32.
4. The resulting 247 bp fragments were gel purified as described in Example 8. These fragments each contain a Pac I cohesive sequence at the 5' end and a Pst I cohesive sequence at the 3' end.
5. The 247 bp fragments were amplified by Polymerase Chain Reaction in a volume of 50 µL with the following components: 250 µM dNTP; 0.2 µM each primers JE50 and JE51; about 50 ng template fragment; 5 µl 10×Pfu reaction buffer (Stratagene), and 1 µl Pfu polymerase (Stratagene). Reactions were run in a Perkin-Elmer 9600 thermocycler with 30 sec. denaturation at 95° C., 30 sec. 60° C. annealing, and 30 sec. 72° C. extension for 25 cycles.
6. The amplification products were purified using the Promega Wizard PCR Cleanup kit according to manufacturer's instructions.

TABLE 4

| fragment # | oligo-nucleotides | description |
|---|---|---|
| 1 | 21/22 | Pac I --> Dra III fragment for amino terminal di-alpha fusion |
| 2 | 23/24 | Dra III --> 1/3 COMP pentamerization domain gene |
| 3 | 25/26 | 1/3 --> 2/3 COMP pentamerization domain gene |
| 4 | 27/28 | 2/3 --> Blp I COMP domain gene with cysteines (wild type) |
| 5 | 29/30 | 2/3 --> Blp I COMP domain genes with 2 Cys-->Ala mutations |
| 6 | 31/32 | Blp I --> Pst I fragment for amino terminal di-alpha fusion |
| 7 | 33/34 | Blp I --> BspE I fragment for carboxy terminal dialpha fusion |
| 8 | 48/49 | Spe I --> Dra III fragment for carboxy terminal dialpha fusion |

7. The purified fragments were digested witih Pac I and Pst L and gel purified.

Cloning: 20 μg pSGE1010 were digested with Pac I and Pst I. The ~4800 bp fragment was gel purified and dissolved in H₂O to a concentration of approximately 200 ng per μl. The synthetic DNA fragments from Assembly step 7 were ligated with the pSGE1010 vector fragment. Ligations were introduced into competent DH5α cells obtained from BRL by transformation.

Transformation procedure: 50 μl frozen competent cells in 1.7 ml microfuge tube were thawed on ice. Approximately 1 μl of a ligation mix was added. The mixture was held 30 minutes on ice, heated to 37° C. for 45 seconds, and returned to ice for 2 minutes. 950 μl room temperature LB was added to each mixture, and the culture placed at 37° C. with shaking for one hour. 100 μl aliquots of the culture were plated on LB+15 μg/ml tetracycline plates and incubated overnight at 37° C.

Transformants were screened by restriction analysis for the correct size recombinant fragment; in addition, unique internal restriction sites have been engineered into the COMP coding sequence for diagnostic purposes. The gene containing cysteines contains an Nsi I site and can be differentiated from the Cys→Ala mutant, which does not contain an Nsi I site by restriction analysis.

Confirmation of the DNA sequence was accomplished using the USB Sequenase v. 2 kit according to manufacturer's instructions.

The N-terminal COMP-dialpha expression plasmids were designated pSGE1308 (WT COMP) and pSGE1309 (cys—alaCOMP).

Plasmids pSGE1308 and 1309 contain the Presbyterian (N108K) beta globin. Two additional plasmids were constructed substituting the Providence (K82D) beta globin mutant for the Presbyterian beta. Plasmid pSGE768, which contains the K82D beta globin gene and the dialpha globin gene in the 720 plasmid background, was digested with Bam HI and BspEI, and the large fragment gel purified. Plasmids pSGE1308 and pSGE1309 were digested with BamHI and BspEI, and the fragments containing the COMP-dialpha genes gel purified. The 1308 and 1309 fragments were ligated with the pSGC769 fragment containing the K82D beta globin gene. The resulting plasmids were verified by sequence analysis, and designated pSGE1351 (WTCOMP) and pSGE1352 (cys→ala COMP).

Carboxy terminal fusion:

pSGE 1010 was digested with Spe I and BspE I and the large fragment gel purified. From the amino terminal fusion plasmid described above, the Dra III-Blp I fragments (with and without cysteines) were gel purified and ligated with annealed, phosphorylated synthetic fragments 33/34 and 48/49, generating a Spe I-BspE I fragment. The gel purified fragments were ligated with the 1010 vector to form two plasmids encoding two carboxy terminal dialpha-COMP domain fusion proteins, one the COMP containing cysteines, and one the Cys→Ala mutant COMP sequence.

To increase yield and to introduce cloning sites for sequence analysis from an intermediate vector, the SpeI-XbaI fragment was amplified by PCR using the Perkin-Elmer AmpliTaq kit according to manufacturer's instructions. Primers JE64 and JE55 were used at a concentration of about 0.5 uM. PCR conditions were:

95° C. 15 gec, 66° C. 15 sec; 72° C. 30 sec, 2 cycles. The amplified product was gel purified, digested with HindIII and BamHI, and ligated with BamHI-HindIII digested pBCSK+ (Stratagene). The ligated DNA was transformed into DH5α competent cells and the transformants screened by sequence analysis using the Amplicycle DNA sequencing kit (Perkin-Elmer) according to manufacturer' instructons, The correct fragment was isolated by digesting with SpeI and XbaI and gel purifying the COMP-dialpha fragment. Plasmid pSGE1307, a derivative of pSGE1004, was digested with SpeI and XbaI and the large fragment was gel purified. The two fragments were ligated and transformed into E. coli strain 1675. The resulting plasmid and strain were designated pSGE1143 and SGE2944, respectively.

The cys→ala C-terminal dialpha-COMP fusion was constructed as follows;

The Blp I-DraII fragment from pSGE1309 was amplified using the AmpliTaq kit and primers JE64 and JE65 (0.5 μM each). The PCR were run in a 2-phase cycle:

95° C. 15 gec, 48° C. 15 sec, 72° C. 15 sec, 15 cycles, then 95° C. 15 sec, 55° C. 15 sec, 72° C. 15 sec, 20 cycles. The amplified product from this reaction was purified over a PCR cleanup spin column (Qiagen), and reamplied as above with primers JE64 and JE66. The amplified DNA fragments were purified over a spin column (Wizard PCR cleanup, Promega), digested with Spe I and Xba I, and gel purified.

The gel purified fragment was ligated with the large purified fragment of pSGE1307 described above, and transformed into 9CF1679. A torrTct dialpha-cys→alaCOMP fusion clone was identified by sequence analysis, and designated pSGE1312. The transformed strain was designated SGE2810. Strains SGE2944 and SGE2810 express the dialpha fusion with the Presbyterian beta globin.

The C-terminal dialpha-COMP fusion genes were cloned into plasmid pSGE768 as described above to co-express with the Providence (K82D) beta globin. The C-terminal dialpha-COMP with Providence beta are WT COMP fusion: pSGE1314/SGE2813; cys→alaCOMP fusion: pSGE1315/SGE2814.

The change from the Presbyterian beta to the Providence (K82D) beta did not have much effect on expression of the N-terminal constructs; it did however increase expression of the C-terminal contructs from <1 g/L to >1.4 g/L.

Example 10 rHb1.1-avidin hybrid protein and coupling with biotinylated dendrimers.

Production of the rHb1.1-avidin hybrid protein.

A synthetic gene encoding avidin is constructed based on the primary amino add sequence published by Livnah et al. (1993, Proc. Natl. Acad. Sci. 90: 5076). Codon usage reflects usage in highly expressed genes in E. coli. The synthetic gene is cloned into a suitable E. coli expression vector, such as the one described in Example 4, and site-directed mutagenesis by any convenient method used to generate mutations in the avidin gene which disrupt tetramerization without affecting biotin binding. For example, regions important for tetramerization (Lys45-Thr55, Gln61-Asn69, Thr76, Val78, Thr80-Gln82, Leu93-Met96 and Leu98-Ser102) are randomly mutated and ~1000 clones which still retain biotin binding activity are rescreened for loss of tetramerization. Biotin binding can be assayed by probing colonies with biotinylated-horseradish peroxidase. Tetramerization can be determined by separating the proteins using native gel electrophoresis, transferring the proteins to nitrocellulose and probing with biotinylated-horseradish peroxidase. A gene encoding a protein exhibiting both biotin binding and the inability to form multimers is fused to either the 5' or 3' end of the dialpha globin gene in the E. coli expression vector. Expression of this construct produces an avidin-dialpha globin which associates with two beta globins to form an avidin-rHb1.1.

Production of biotinylated dendrimers.

Biotin is coupled to an activated matrix such that a discrete number of biotin moieties, i.e. 3, 4, 5 etc. are joined together while remaining accessible to avidin. For example, N-hydroxy succinimide activated biotin can be directly coupled to dendrimers which possess terminal amino groups (Dendritech Inc., Midland, Michigan) by reacting NHS-LC-biotin (Pierce Chemical Co.) with the dendrimers in an aqueous buffer. The reaction is controlled so that discrete numbers of biotins are crosslinked to each dendrimer and the dendrimer-biotin complexes purified by any appropriate method such as, for example, reverse phase high pressure liquid chromatography.

Coupling of avidin-rHb1.1 and biotinylated dendrimers.

Coupling of the avidin-rHb1.1 and a suitable derivatized dendrimers, such as biotinylated dendrimers, is accomplished by mixing the avidin-rHb1.1 in an ~5:1 molar ratio of avidin-rHb1.1:biotin. This produces a biotinylated dendrimer with 100% of the biotin moieties saturated with avidin-rHb1.1. The unreacted avidin-rHb1.1 is then removed by diafiltration and can be salvaged for used in future coupling reactions.

Example 11

P22 Arc-dialpha fusion.

The P22 Arc repressor forms a dimer in solution, and was cloned as a linker fusing two dialpha globin genes so that assembly of the dimerizing domain would form a tetrameric hemoglobin. The cloning strategy was similar to that described for the internal GCN4 fusion described in Example 4. Molecular biology techniques were the same as used in Example 9 unless noted otherwise.

The Arc domain gene encodes the following protein:

MKGMSKMPQFNLRWPREVLDLVRKVAEENGRSVNSEIYQRVMESPKKEGRIGA (SEQ. ID. NO. 92)

The Arc protein was fused between two dialpha globins via identical peptide linkers at end end of Arc; GGSGGSGGSGG (SEQ. ID. NO. 93)

The synthetic Arc-linker cloning cassette was assembled from the following oligonucleotides:

EV152:

5' CTATTTATATTTGAATTCCTGCAGGCCACCGGAGCCACCGGAGCCGCCAG 3' (SEQ. ID. No 94)

EV153

5' ACTATAAAAAGGATCCACTAGTGGTGGTTCTGGTGGTTCTGGTGGTTCTGGTGGTATGAAAGG 3' (SEQ. ID. NO. 95)

EV154A

5 GGTTCTGGTGGTATGAAAGGAATGAGCAAAATGCCGCAGTTCATTTGCGGTGGCCTAGAGAAGTATTGG 3' (SEQ. ID. NO. 96)

EV154B

5' GCCACCGCAAATTGAACTGCGGCATTTTTGCTCATTCCAATCATACCACCAGAACC 3' (SEQ. ID. NO. 97)

EV155A

5' ATUTGGTACGCAAGGTAGCGGAAGAGAATGGTCGGTCTGTTAAATCTGAGATTTATCAGCGAGTA 3' (SEQ. ID. NO. 98)

EV155B

5' AGAATTAAACAGACCGACCATTCTCTTCCGCTACCTTGCGTACCAAATCCAAATAOTTCTCTAG 3' (SEQ. ID. NO. 99)

EV156A

5' ATGGAAAGCTAAGAAGGAAGGGCGCATTGGCGOGGGTGGCTCTGGCGGCTCCGGTGGC 3' (SEQ. ID. NO. 100)

EV156B

5' BCACCGGAGCCGCCAGAGWCACCGCGCGCATGCGCCCTTCTTAAAGGCTTTCCATTACTCGCTGATAAATC 3' (-. ID. NO. 101)

Complememtary oligonucleotides were gel purified, phosphorylated, and annealed to form fragments EV154AB, EV155AB, and EV156AB. The three fragments were ligated together, gel purified, and amplified using primers EV153 and EV152 (0.5 $\mu$M each) and the AmpliTaq PCR kit (Perkin-Elmer) according to manufacturer's instructions. PCR cycling conditions were: 95° C. 15 sec, 60° C. 15 see, 72° C. 30 sec. 25 cycles in a Perkin-Elmer 9600 thermocycler. The PCR amplified product was gel purified and cloned into pBC SK+ as a BamHI-HindIII fragment for sequence analysis. The correct linker-Arc-linker domain was excised from pBC SK+ as an Spe I-Pst I fragment and ligated into Spe I-Pst I digested pSGE1000, generating plasmid pSGE1146 which Contains the internal Arc-di-dialpha fusion coexpressed with Presbyterian beta globin. This plasmid was transformed into SGE1464 to generate strain SGE2953.

The BamHI-BspEI fragment from pSGE1146 containing the Arc-di-dialpha genes was purified and ligated with the BamHI-BspEI from pSGE768 containing the Providence (KA2D) beta globin gene. The resulting plasmid pSGE1148 transformed into SGE1675 generated strain SGE2955, which expresses Arc-di-dialpha with Providence beta globin.

Example 12

Di-alpha P22 Mnt repressor fusion.

The C-terminal domain of the bacteriophage P22 Mnt repressor (residues 52–82), which forms an independent alpha-helical tetramerization domain, was fused to the C-terminus of dialpha globin. The peptide sequence of the Mnt tetramerization domain is:

SPVTGYRNDAERLADEQSELVKKMVFDTLKDLYKKTT (SEQ. ID. NO. 102)

The domain was fused to dialpha globin via the pepfide linker: GGSGGSGGSGG (SEQ. ID. NO. 103)

The linker-domain coding sequence was cloned as a synthetic DNA fragment. Cloning strategy and molecular biology techniques were essentially as described in Example 9 unless otherwise noted.

The synthetic gene was assembled from the following oligonudeotides:

JEMS1 5' GGTTCTGGTGGTTCTGGTGGTTCTGGTGGTTCTCCGGTTACCGGT 3' (SEQ. ID. NO.104)

JEMS2 5' TACCGTAACGACGCTGAACGTCTGGCTGACGAACAGTCTGAACTG 3' (SEQ. ID. NO. 105)

JEMA1 5' ATTAGGTGGTCTTCTTGTACAGGTCTTTCAGGGTGTCGAAAACCA 3' (SEQ. ID. NO. 106)

JEMA2 5' TCTTCTTAACCAGTTGAGACTGTTCGTCAGCCAGACGTTCAGCGT 3' (SEQ. ID. NO. 107)

JEMA3 5' GTTMGAAGATGGTTTTCGACACCCCTGAAAGACCTGTACAAGAAGACCACCTAAT 3' (SEQ. ID. NO. 108)

JEMA3 5' CGTTACGGTAACCGGTAACCGGAGAACCACCAGAACCACCAGAACCACCAGAACC 3' (SEQ. ID. NO. 109)

JE6 5 CGCGCGATCCACTAGTAAATACCGTGGTGGTTCGTCTGGTGGTTCTGGTGG 3' (SEQ. ID. NO. 110)

JE67 5' CGCGTATATACGMGCTTTCTAGATTATTAGGTGGTCTTCTTGTACAGG 3' (SEQ. ID. NO. 111)

Complementary oligonucleotides were gel purified, phosphorylated and annealed to form fragments JEMS1/MA3, JEMS2/MA2, and JEMS3/MA1. The three fragments were ligated together and the 150 bp fragment gel purified. The gel purified fragment was amplified with primers JE66 and JE67 (1.0 µM each) using the AmpliTaq PCR kit (Perkin-Elmer) according to manufacturer's instructions. The PCR conditions were: 95° C. 15 sec, 50° C. 15 sec, 72° C. 15 sec, 25 cycles. The amplified product was spin column purified (Qiagen) and digested with Spe I and Xba I. The digested fragment was gel purified and ligated with Spe I-Xba I digested pSGE1307 as described in Example 9 and transformed into competent SGE1675. A transformed plasmid containing the correct dialpha-Mnt domain coding sequence was identified by sequence analysis (ABI automated sequencer model 373A). This plasmid, which coexpresses the dialpha-Mnt fusion with Presbyterian beta globin, was designated pSGE1317, and the strain SGE2817.

The BamHI-BspeI fragment from pSGE1317 containing the dialpha-Mnt gene was gel purified and ligated with the purified BamHI-BspeI fragment from pSGE768 containing the Providence (K82D) beta globin gene. The resulting plasmid was designated pSGE1319, and was transformed into SGE1675 to generate strain SGE2819. This strain produces dialpha-Mnt fusion protein coexpressed with Providence (K82D) beta globin.

Example 13
Globins Containing Binding Domains.

All strains were grown in a Biolafitte 100 L fermentor using the DM59 medium described in the patent. Induction was performed at 28 deg C for 16 hr.

Following induction, the fermentation broth was chilled then harvested as described below. All of the strains described in this addendum contain the beta globin Providence mutation. This mutation has been shown to increase the soluble expression yield of rHb, and was incorporated here to aid rapid recovery and purification of preclinical material. In some strains other beta globin mutations (e.g. Presbyterian) are also present.

A. SGE 955

SGE 955 is an rHb containing a dialpha-GCN4-dialpha globin with the Presbyterian mutation in the beta globin. SGE 955 is designed to yield a tetra-rHb.

(i) Recovery

A Niro Panda™ cell disruption device (Niro Hudson, Inc. Hudson, Wis.) was used for homogenization of the fermentation broth. Cells were lysed by a single passage through the homogenizer which was set at 800 bar. The lysate was sparged with CO gas, heated to 72° C. for 11 sec. The pH of the lysate was adjusted to pH 8 with sodium hydroxide, sufficient $Zn(OAc)_2$ was added to make the solution 2–4 mM in $Zn(OAc)_2$, flocculating agent (Magnafloc 573-C, American Cyanamid, Wayne N.J.) was added to 0.25% (v/v) and the lysate was clarified by solution 24 mM in $Zn(OAc)_2$, flocculating agent (Magnafloc 573-C, American Cyanamid, Wayne N.J.) was added to 0.25% (v/v) and the lysate was clarified by centrifugation. The clarified lysate was then filtered in a CUNO (Meriden, Conn.) apparatus.

(ii) Purification:

All solutions were 4° C. and were adjusted to the correct pH at 4° C. 2 L of Chelating Sepharose fast flow resin (Pharmacia, Piscataway, N.J.) was prepared by washing with 4 column volumes (CV) of distilled water. The resin was charged with 2 to 3 CV of 20 mM $Zn(OAc)_2$ followed by 2 to 3 CV of 200 mM NaCl. The filtered, clarified lysate was loaded onto the column and washed with 1 CV of 20 mM Tris•HC 50 mM NACL ph 8.0; 2 CV of 20 mM Tris•HO 500 mM NaCl pH 8.0; 2 CV of 20 mM Tris•HCl 50 mM NaCl pH 8.0; 10 CV of 10 mM imidazole 50 mM NaCl pH 7.2; 4 CV of 20 mM sodium phosphate 50 mM NaCl pH 6.5. The bound protein was then eluted with 20 mM Tris HCl 15 mM EDTA pH 8.0. The purified protein solution was then concentrated to approximately 20 mg/mL and buffer exchanged with 6–8 CV of 20 mM Tris•HCl, pH 8.8 using a Filtron Technology Corp. (Northborough, Mass.) diafiltration apparatus equipped with 30 kDa MWCO membranes to yield 1.5 gm of partially purified protein. The different size hemoglobins were separated by size exclusion chromatography (SEC) on Pharmacia (Piscataway, N.J.) S-200 and S-300 columns linked in parallel.

Each SEC column was packed with approximately 6.5 L of the designated resin.

The columns were eluted using 10 mM phosphate pH 7.4, 150 mM NaCl (PBS) as the mobile phase. 7.5 gm of protein were loaded onto the columns. Appropriate fractions were pooled and buffer exchanged into 20 mM Tris•HCl pH 8.8 by diafiltration, to yield 3.0 gm of the oligomeric rHb. The SEC-purified protein was bound to a thin bed IMAC column charged with $Zn(OAc)_2$, then reoxygenated by passing highly oxygenated buffer over the immobilized rHb for 7 hr at 0 deg C. Following reoxygenation, the protein was eluted with EDTA as described above and concentrated and diafiltered into 20 mM Tris•HCl pH 8.9. The oxygenated protein was further purified by anion exchange chromatography on Q-SEPHAROSE resin (Pharmacia, 300 mL column). 2.5 gm of protein were loaded onto the column in 20 mM Tris•HCl pH 9.0. The column was washed with 3 CV 20 mM Tris•HCl pH 9.0 then eluted with 20 mM Bis-Tris pH 6.8. The protein (1.5 gm) was formulated for preclinical studies in endotoxin-free PBS by diafiltration in a clean environment at a final concentration of 31 mg/mL.

(iii) Protein analysis and characterization.

The globin chains of the final purified material were separated by C4 reverse phase high performance liquid chromatography (RP-HPLC) on a Hewlett Packard model 1090 HPLC equipped with a Vydac 5µ, 0.46×25 cm C4 column using a gradient of acetonitrile (ACN) in water (both containing 0.1% trifluoroacetic add) as the mobile phase. The 75 min gradient elution was established as follows: 3 min at 30% ACN, a linear gradient from 30–37% ACN over 12 min, a linear gradient from 37–50% ACN over 60 min. The C4 chromatogram showed four prominent peaks eluting at 15.7 min, 40.8 min, 59.9 10 min, and 65.4 min respectively. The separated globins were analyzed by electrospray mass spectroscopy (Vestec, Inc., Houston, Tex.).

ESMS analysis showed that the peak eluting at 15.7 min was heme. The peak eluting at 40.8 min was identified as beta-globin (observed mass=15913, calculated mass–15913). The peak eluting at 65.4 min was identified as the dialpha-GCN4-dialpha globin (observed mass=66092, calculated mass=66036). The broad peak eluting at 59.9 min is apparently a heterogenous mixture of fragments of the alpha fusion protein which include the GCN4 domain and linker regions but only one dialpha globin. This peak comprises roughly 23% of the alpha globin species.

Analytical SEC performed on Pharmacia SUPEROSE-12 and SUPEROSE-6 columns linked in series with PBS as the mobile phase showed that the SGE 955 protein eluted as a larger protein than a single recombinant hemoglobin molecule. The retention times on this column for 955 protein and rHb1.1 were 48.8 min and 60.1 min respectively. Particle sizes of purified hemoglobins were determined by laser light scattering using a NICOMP 370 HPL Submicron Particle Sizer (PSS, Santa Barbara, Calif.). Samples were analyzed at 10 mg/mL in PBS. The mean diameter of 955 protein was 13.2 nm (mono-rHb has a mean diameter of 6.0 nm).

The oxygen affinity and cooperativity of the purified protein were determined at 37° C. using a Hemox analyzer (TCS Medical Products, Southampton, Pa.) using the methods described in issued U.S. Pat. No. 5,028,588. The observed $P_{50}$ was 27 torr with an $n_{max}$ of 2.1.

B. SGE 2795

SGE 2795 is an rHb containing a dialpha-GCN4-dialpha globin with Presbyterian and Providence (K82D) mutations in the beta globin. The protein differs from that of SGE 955 by the presence of the Providence mutation in each beta globin subunit. The protein of SGE 2795 is designed to yield a tetra-rHb.

(i) Recovery:

Performed as described above in part A for SGE 955

(ii) Purification:

All solutions were 4° C. and were adjusted to the correct pH at 4° C. 2 L of Chelating Sepharose fast flow resin (Pharmacia, Piscataway, N.J.) was prepared by washing with 4 column volumes (CV) of distilled water. The resin was charged with 2 to 3 CV of 20 mM $Zn(OAc)_2$ followed by 2 to 3 CV of 200 mM NaCl. The filtered, clarified lysate was loaded onto the column and washed with 1 CV of 20 mM Tris•HCl 50 mM NaCL pH 8.0; 2 CV of 20 mM Tris•HCl 500 mM NaCl pH 8:0; 2 CV of 20 mM Tris•HCl 50 mM NaCl pH 8.0; 10 CV of 10 mM imidazole 50 mM NaCl pH 7.2; 4 CV of 20 mM sodium phosphate 50 mM NaCl pH 6.5. The bound protein was then eluted with 20 mM Tris•HCl 15 mM EDTA pH 8.0. The purified protein solution was then concentrated to approximately 20 mg/mL and buffer exchanged with 6–8 CV of 20 mM Tris•HCl, pH 8.8 using a Filtron Technology Corp. (Northborough, Mass.) diafiltration apparatus equipped with 30 kDa MWCO membranes to yield 9 gm of partially purified protein. The different sized hemoglobins were separated by size exclusion chromatography (SEC) on Pharmacia (Piscataway, N.J.) S200 and S300 columns linked in parallel. Each SEC column was packed with approximately 6.5 L of the designated resin. The columns were eluted using 10 mM phosphate pH 7.4, 150 mM NaCl (PBS) as the mobile phase. 6.5 gm of protein were loaded onto the columns. Appropriate fractions were pooled and buffer exchanged into 20 mM Tris•HCl pH 8.8 by diafiltration, to yield 3.6 gm of the oligomeric rHb. The SEC-purified protein was bound to a thin bed IMAC column charged with $Zn(OAc)_2$ then reoxygenated by passing highly oxygenated buffer over the immobilized rHb for 7 hr at 0 deg C. Following reoxygenation, the protein was eluted with EDTA as described above and concentrated and diafiltered into 20 mM Tris•HCl pH 8.9. The oxygenated protein was further purified by anion exchange chromatography on Q-SEPHAROSE resin (Pharmacia, 700 mL column). 5.4 gm of protein were loaded onto the column in 20 mM Tris•HCl pH 8.9. The column was washed with 3 CV 20 mM Tris•HCl pH 8.9 then eluted with 20 mM Bis-Tris pH 6.8, 15 mM NaCl. The protein (3.0 gm) was formulated for preclinical studies in endotoxin-free PBS by diafiltration in a dean environment at a final concentration of 50 mg/mL.

(iii) Protein analysis and characterization.

The globin chains of the final purified material were separated by C4 reverse phase high performance liquid chromatography (RP-HPLC) on a Hewlett Packard model 1090 HPLC equipped with a Vydac 5 $\mu$ 0.46×25 cm C4 column using a gradient of acetonitrile (ACN) in water (both containing 0.1% trifluoroacetic acid) as the mobile phase. The 75 min gradient elution was established as follows: 3 min at 30% ACN, a linear gradient from 30–37% ACN over 12 min, a linear gradient from 37–50% ACN over 60 min. The C4 chromatogram showed three prominent peaks eluting at 27.4 min, 42.4 min, and 61.1 min respectively. In addition, a broad peak comprising less than 15% of the area of the 61.1 min peak was also observed. The separated globins were analyzed by electrospray mass spectrogeopy (ESMS)(Vestec, Inc., Houston, Tex.).

ESMS analysis showed that the peak eluting at 27.4 min was heme. The peak eluting at 42.4 min was identified as beta-globin (observed mass=15902, calculated mass= 15899). The peak eluting at 61.1 min was identified as the dialpha-GCN4-dialpha globin (observed mass=66069, calculated mass=66036). peak eluting at 56.8 min is apparently a heterogenous mixture of fragments of the alpha fusion protein which include the GCN4 domain and linker regions but only one dialpha globin.

Analytical SEC performed on Pharmacia SUPEROSE-12 and SUPEROSE-6 columns linked in series with PBS as the mobile phase showed that the SGE 2795 protein eluted as a larger protein than a single recombinant hemoglobin molecule. The retention times on this column for 2795 protein and rHb1.1 were 48.0 min and 60.1 min respectively. Particle sizes of purified hemoglobins were determined by laser light scattering using a NICOMP 370 HPL Submicron Particle Sizer (PSS, Santa Barbara, Calif.). Samples were analyzed at 10 mg/mL in PBS. The mean diameter of 2795 protein was 13.8 nm (mono-rHb has a mean diameter of 6.0 ni).

The oxygen affinity and cooperativity of the purified protein were determined at 37° C. using a Hemox analyzer (TCS Medical Products, Southampton, Pa.) using the methods described in issued U.S. patent 5,028,588. The observed $P_{50}$ was 39 torr with an $n_{max}$ of 2.0.

(iv) Determination of circulating halflife.

Male Sprague-Dawley rats were chronically instrumented with venous catheters 4–6 days before experimentation. Top-load doses of 350 mg/kg of rHb were administered via intravenous infusion at a rate of 0.5 mL/min to six rats each in experimental and control (received rHb1.1) groups. Blood (0.3 mL) was collected from the tail vein into heparanized tubes and centrifuged to separate out plasma at 0, 0.5, 1, 2, 4, 8, 12 and 24 hrs post infusion. Plasma rHb concentration was determined by the cyanomet-Hb method using a Hewlett-Packard model 8452A spectrophotometer (extinction coefficients were determined independently by iron analysis). Curves were fit to data using single exponential equations. rHb1.1 and SGE 2795 had the same observed halflife of 2.8 hrs.

C. SGE 2948 (dialpha-p53 fusion)

SGE 2948 is an rHb containing a dialpha globin fused at the C-terminus to the tetramerizing domain of human p53. The beta globin contains the Providence (K82D) mutation. SGE 2948 protein is designed to yield a tetra-rhb and differs from the SGE 2802 protein only in the beta globin sequence.

(i) Recovery

Performed as described above except that the lysate was heated to 82° C. rather than 72° C.

(ii) Purification:

All solutions were 4° C. and were adjusted to the correct pH at 4° C. 3 L of Chelating Sepharose fast flow resin (Pharmacia, Piscataway, New Jersey) was prepared by washing with 4 column volumes (CV) of distilled water. The resin was charged with 2 to 3 CV of 20 mM $Zn(OAc)_2$ followed by 2 to 3 CV of 200 mM MaCl. The filtered, clarified lysate was loaded onto the column and washed with 1 CV of 20 mM Tris•HCl 50 mM NaCL pH 8.0; 2 CV of 20 mM Tris•HCl 500 mM NaCl pH 8.0; 2 CV of 20 mM Tris•HCl 50 mM NaCl pH 8.0; 10 CV of 10 mM imidazole 50 mM NaCl pH 7.2; 4 CV of 20 mM sodium phosphate 50 mM NaCl pH 6.5. The bound protein was then eluted with 20 mM Tris•HCI 15 mM EDTA pH 8.0. The purified protein solution was then concentrated to approximately 20 mg/mL and buffer exchanged with 6–8 CV of 20 mM Tris•HCl, pH 8.8 using a Filtron Technology Corp. (Northborough, Mass.) diafiltration apparatus equipped with 30 kDa MWCO membranes to yield 85 gm of partially purified protein. The different size hemoglobins were separated by size exclusion chromatography (SEC) on Pharmacia (Piscataway, N.J.) S-200 and S-300 columns linked in parallel. Each SEC column was packed with approximately 6.5 L of the designated resin. The columns were eluted using 10 mM phosphate pH 7.4, 150 mM NaCl (PBS) as the mobile phase. 7.0 gm of protein were loaded onto the columns. Appropriate fractions were pooled and buffer exchanged into 20 mM Tris-HCl pH 8.8 by diafiltration, to yield 3.1 gm of the oligomeric rHb. The SEC-purified protein was bound to a thin bed IMAC column charged with $Zn(OAc)_2$, then reoxygenated by passing highly oxygenated buffer over the immobilized rHb for 7 Lr at 0 deg C. Following reoxygenation, the protein was eluted with EDTA as described above and concentrated and diafiltered into 20 mM Tris•HCl pH 8.9. The oxygenated protein was further purified by anion exchange chromatography on Super-Q 650 C resin (TosoHaas, Montgomeryville, Pa., 400 mL column). 6.0 gm of protein were loaded onto the column in 20 mM Tris•HC pH 8.9. The column was washed with 8 CV 20 mM Tris*HO pH 7.6 then eluted with 20 mM Bis-Tris pH 6.8, 15 mM NaCl. The protein (2.4 gm) was formulated for preclinical studies in endotoxin-free PBS by diafiltration in a clean environment at a final concentration of 48 mg/mL.

(iii) Protein analysis and characterization.

The globin chains of the final purified material were separated by C4 reverse phase high performance liquid chromatography (RP-HPLC) on a Hewlett Packard model 1090 HPLC equipped with a Vydac 5 $\mu$ 0.46×25 cm C4 column using a gradient of acetonitrile (ACN) in water (both containing 0.1% trifluoroacetic acid) as the mobile phase. The 75 min gradient elution was established as follows: 3 min at 30% ACN, a linear gradient from 30–37% ACN over 12 min, a linear gradient from 37–50% ACN over 60 min. The C4 chromatogram showed three prominent peaks eluting at 25.4 min, 45.1 min, and 54.4 min respectively. The separated globins were analyzed by electrospray mass spectroscopy (Vestec, Inc., Houston, Tex.).

ESMS analysis showed that the peak eluting at 25.4 min was heme. The peak eluting at 45.1 min was identified as beta-globin (observed mass=15886, calculated mass=15886). The peak eluting at 54.4 min was identified as the dialpha-p53 globin (observed mass=36337, calculated mass=36280).

Analytical SEC performed on Pharmacia SUPEROSE-12 and SUPEROSE-6 columns linked in series with PBS as the mobile phase showed that the SGE 2948 protein eluted as a larger protein than a single recombinant hemoglobin molecule. The retention times on this column for 2948 protein and rHb1.1 were 49.2 min and 60.1 min respectively.

The oxygen affinity and cooperativity of the purified protein were determined at 37° C. using a Hemox analyzer (TCS Medical Products, Southampton, Pa.) using the methods described in issued U.S. Pat. No. 5,028,588. The observed $P_{50}$ was 12.9 torr with an $n_{max}$ of 2.05.

(iv) Determination of circulating halflife.

Male Sprague-Dawley rats were chronically instrumented with venous catheters 46 days before experimentation. Topload doses of 350 mg/kg of rHb were administered via intravenous infusion at a rate of 0.5 mL/min to six rats each in experimental and control (received rHb1.1) groups. Blood (0.3 mL) was collected from the tail vein into heparanized tubes and centrifuged to separate out plasma at 0, 0.5, 1, 2, 4, 8, 12 and 24 hrs post infusion. Plasma rHb concentration was determined by the cyanomet-Hb method using a Hewlett-Packard model 8452A spectrophotometer (extinction coefficients were determined independently by iron analysis). Curves were fit to data using single exponential equations. rHb1.1 and SGE 2948 had observed halflives of 2.8 hr and 4.9 hr, respectively.

D. SGE 2813 (di-dialpha-COMP fusion)

SGE 2813 is an rHb containing a dialpha globin fused at its C-terminus to the pentamerizing domain from rat cartilage oligomeric matrix protein (COMP). The beta globin in this strain contains the Providence (K82D) mutation. SGE 2813 is designed to yield a penta-rHb. There are two Cys residues in te COMP pentamerizing domain. These Cys residues may be present in the native structure to provide covalent stabilization of the pentamer.

(i) Recovery

Performed as described above, except the lysate was heated to 82° C. rather than 72° C.

(ii) Purification.

All solutions were 4° C. and were adjusted to the correct pH at 4° C. 3 L of Chelating Sepharose fast flow resin (Pharmacia, Piscataway, New Jersey) was prepared by washing with 4 column volumes (CV) of distilled water. The resin was charged with 2 to 3 CV of 20 mM $Zn(OAc)_2$ followed by 2 to 3 CV of 200 mM NaCl. The filtered, clarified lysate was loaded onto the column and washed with 1 CV of 20 mM Tris•HC 50 mM NaCL pH 8.0; 2 CV of 20 mM Tris•HCl 500 mM Naa pH 8.0; 2 CV of 20 mM Tris•HCl 50 mM NaCl pH 8.0; 10 CV of 10 mM imidazole 50 mM NaCl pH 7.2; 4 CV of 20 mM sodium phosphate 50 mM NaCl pH 6.5. The bound protein was then eluted with 20 mM Tris•HCl 15 mM EDTA pH 8.0. The purified protein solution was then concentrated to approximately 20 mg/mL and buffer exchanged with 6–8 CV of 20 mM Tris-HCl, pH 8.8 using a Filtron Technology Corp. (Northborough, Mass.) diafiltration apparatus equipped with 30 kDa MWCO membranes to yield 50 gm of partially purified protein. The different size hemoglobins were separated by size exclusion chromatography (SEC) on Pharmacia (Piscataway, N.J.) S-200 and S-300 columns linked in parallel. Each SEC column was packed with approximately 6.5 L of the designated resin. The columns were eluted using 10 mM phosphate pH 7.4, 150 mM NaCl (PBS) as the mobile phase. 10 gm of protein were loaded onto the columns. Appropriate fractions were pooled and buffer exchanged into 20 mM Tris•HCl pH 8.8 by diafiltration, to yield 4.3 8 m of the oligomeric rHb. The SEC-purified protein was bound to a thin bed IMAC column charged with $Zn(OAc)_2$, Men reoxygenatad by passing highly oxygenated buffer over the immobilized rHb for 7 hr at 0 deg C. Following reoxygenation, the protein was eluted with EDTA as described above and concentrated and dialfiltered into 20 mM Tris•HCl pH 8.9. The oxygenated protein was further purified by anion exchange chromatography on Super-Q 650C resin (TosoHaas, Montgomeryville, Pa., 500 mL column). 9.0 gin of protein were loaded onto the column in 20 mM Tris•HCl pH 8.9. The column was washed with 4 CV 20 mM Tris•HCl pH 7.6 then eluted with 20 mM Bis-Tris pH 6.8, 15 mM NaCl. The protein (4.6 gm) was formulated for preclinical studies in endotoxin-free PBS by diafiltration in a clean environment at a final concentration of 52 mg/mL.

(iii) Protein analysis and characterization.

The globin chains of the final purified material were separated by C4 reverse phase high performance liquid chromatography (RP-HPLC) on a Hewlett Packard model 1090 HPLC equipped with a Vydac 5 μ 0.46×25 cm C4 column using a gradient of acetonitrile (ACN) in water (both containing 0.1% tifluoroacetic add) as the mobile phase. The 75 min gradient elution was established as follows: 3 min at 30% ACN, a linear gradient from 30–37% ACN over 12 min, a linear gradient from 37–50% ACN over 60 min. The C4 chromatogram showed four prominent peaks eluting at 26.5 min, 43.0 min, 59.9 min, and 61.2 min respectively. The separated globins were analyzed by electrospray mass spectroscopy (Vestec, Inc., Houston, Tex.).

ESMS analysis showed that the peak eluting at 26.5 min was heme. The peak eluting at 43.0 min was identified as beta-globin (observed mass=15886, calculated mass=15886). The peaks eluting at 59.9 min and 61.2 min have masses roughly 600 amu larger than expected for the dialpha-COMP globin (observed masses=38672 and 38671, respectively, calculated mass=38076). This extra mass maybe be addition of two glutathione moieties to the globin (recall there are two Cys residues in the COMP sequence).

Analytical SEC performed on Pharmacia SUPEROSE-12 and SUPEROSE-6 columns linked in series with PBS as the mobile phase showed that the SGE 2813 protein eluted as a larger protein than a single recombinant hemoglobin molecule. The retention times on this column for 2813 protein and rHb1.1 were 47.7 min and 60.1 min respectively.

The oxygen affinity and cooperativity of the purified protein were determined at 37° C. using a Hemox analyzer (TCS Medical Products, Southampton, Pa.) using the methods described in granted patent 5,028,588. The observed $P_{50}$ was 5.5 torr wit an $n_{max}$ of 1.3.

(iv) Determination of circulating halflife.

Male Sprague-Dawley rats were chronically instrumented with venous catheters 4–6 days before experimentation. Top-load doses of 350 mg/kg of rHb were administered via intravenous infusion at a rate of 0.5 mL/min to six rats each in experimental and control (received rHb1.1) groups. Blood (0.3 mL) was collected from the tail vein into heparanized tubes and centrifuged to separate out plasma at 0, 0.5, 1, 2, 4, 8, 12 and 24 hrs post infusion. Plasma rHb concentration was determined by the cyanomet-Hb method using a Hewlett-Packard model 8452A spectrophotometer (extinction coefficients were determined independently by iron analysis). Curves were fit to data using single exponential equations. rHb1.1 and SGE 2813 had observed halflives of 2.8 hr and 3.9 hr, respectively.

What is claimed is:

1. A globin comprising an added amino acid sequence, the amino acid sequence comprising a GCN4 binding domain capable of forming oligomers wherein the globin has an altered oxygen binding affinity as compared to normal human alpha or beta globin.

2. The globin of claim 1, wherein the binding domain is fused either directly or through an amino acid linker sequence to the N-terminus or the C-terminus of the globin.

3. The globin of claim 1, wherein the binding domain is a GCN4 derivative.

4. A multimeric hemoglobin, wherein each hemoglobin in the multimeric hemoglobin is comprised of globins, and wherein at least one of the globins in each hemoglobin is the globin of claim 1.

5. The globin of claim 1, wherein the globin is expressed by a recombinant host cell.

6. The globin of claim 5, wherein the recombinant cell is a non-erythrocyte cell.

7. The globin of claim 6, wherein the non-erythrocyte cell is *E. coli*.

8. A composition comprising multimeric hemoglobin, wherein said multimeric hemoglobin is comprised of at least one globin of claim 1.

9. The globin of claim 1 wherein the globin is genetically fused to another globin.

10. The globin of claim 2, wherein the binding domain is a GCN4 derivative.

* * * * *